US012605242B2

(12) United States Patent
Simons et al.

(10) Patent No.: US 12,605,242 B2
(45) Date of Patent: Apr. 21, 2026

(54) METHODS OF FORMING IMPLANTS SUITABLE FOR SOFT TISSUE REPAIR

(71) Applicant: SOFRADIM PRODUCTION, Trevoux (FR)

(72) Inventors: Damien Simons, Lyons (FR); Gaetan Guerin, Lyons (FR); Nizar Bechir, Feyzin (FR)

(73) Assignee: SOFRADIM PRODUCTION, Trevoux (FR)

( * ) Notice: Subject to any disclaimer, the term of this patent is extended or adjusted under 35 U.S.C. 154(b) by 407 days.

(21) Appl. No.: 17/968,615

(22) Filed: Oct. 18, 2022

(65) Prior Publication Data

US 2023/0320832 A1 Oct. 12, 2023

Related U.S. Application Data

(62) Division of application No. 16/666,551, filed on Oct. 29, 2019, now Pat. No. 11,471,257.

(30) Foreign Application Priority Data

Nov. 16, 2018 (EP) .................................... 18206825

(51) Int. Cl.
*A61F 2/00* (2006.01)
*D02G 3/02* (2006.01)
*D02G 3/26* (2006.01)

(52) U.S. Cl.
CPC ............. *A61F 2/0063* (2013.01); *D02G 3/02* (2013.01); *D02G 3/26* (2013.01); *A61F 2210/0004* (2013.01)

(58) Field of Classification Search
CPC ..... D05C 7/08; D05C 7/00; A61F 2002/0068; A61F 2/0063
See application file for complete search history.

(56) References Cited

U.S. PATENT DOCUMENTS

| | | | |
|---|---|---|---|
| 1,187,158 A | 6/1916 | Mcginley | |
| 3,118,294 A | 1/1964 | Van Laethem | |
| 3,124,136 A | 3/1964 | Usher | |
| 3,272,204 A | 9/1966 | Artandi et al. | |

(Continued)

FOREIGN PATENT DOCUMENTS

| | | |
|---|---|---|
| CA | 1317836 C | 5/1993 |
| DE | 19544162 C1 | 4/1997 |

(Continued)

OTHER PUBLICATIONS

Threads Sewing, Sewing Machine Anatomy: How a Stitch is Made, Mar. 11, 2015, YouTube (https://www.youtube.com/watch?v=2681yeSrsM0) (last visited Jan. 31, 2025). (Year: 2015).*

(Continued)

*Primary Examiner* — Patrick J. Lynch

(74) *Attorney, Agent, or Firm* — Weber Rosselli & Cannon LLP

(57) ABSTRACT

Methods of forming implants suitable for hernia or prolapse repair are provided, the implants including an implantable web including a combination of laid yarns and threading yarns and optionally a substrate. The methods include at least laying one or more laid yarns and threading one or more thread yarns.

17 Claims, 24 Drawing Sheets

(56) References Cited

U.S. PATENT DOCUMENTS

| | | | |
|---|---|---|---|
| 3,276,448 A | 10/1966 | Kronenthal | |
| 3,320,649 A | 5/1967 | Naimer | |
| 3,364,200 A | 1/1968 | Ashton et al. | |
| 3,570,482 A | 3/1971 | Shigeru et al. | |
| 4,006,747 A | 2/1977 | Kronenthal et al. | |
| 4,060,081 A | 11/1977 | Yannas et al. | |
| 4,173,131 A | 11/1979 | Melton et al. | |
| 4,193,137 A | 3/1980 | Heck | |
| 4,248,064 A | 2/1981 | Odham | |
| 4,294,241 A | 10/1981 | Miyata | |
| 4,307,717 A | 12/1981 | Hymes et al. | |
| 4,338,800 A | 7/1982 | Matsuda | |
| 4,476,697 A | 10/1984 | Schafer et al. | |
| 4,487,865 A | 12/1984 | Balazs et al. | |
| 4,500,676 A | 2/1985 | Balazs et al. | |
| 4,511,653 A | 4/1985 | Play et al. | |
| 4,527,404 A | 7/1985 | Nakagaki et al. | |
| 4,591,501 A | 5/1986 | Cioca | |
| 4,597,762 A | 7/1986 | Walter et al. | |
| 4,603,695 A | 8/1986 | Ikada et al. | |
| 4,631,932 A | 12/1986 | Sommers | |
| 4,670,014 A | 6/1987 | Huc et al. | |
| 4,709,562 A | 12/1987 | Matsuda | |
| 4,748,078 A | 5/1988 | Doi et al. | |
| 4,759,354 A | 7/1988 | Quarfoot | |
| 4,769,038 A | 9/1988 | Bendavid et al. | |
| 4,796,603 A | 1/1989 | Dahlke et al. | |
| 4,813,942 A | 3/1989 | Alvarez | |
| 4,841,962 A | 6/1989 | Berg et al. | |
| 4,846,815 A | 7/1989 | Scripps | |
| 4,854,316 A | 8/1989 | Davis | |
| 4,867,086 A * | 9/1989 | Vees | D04H 3/10 |
| | | | 428/102 |
| 4,925,294 A | 5/1990 | Geshwind et al. | |
| 4,931,546 A | 6/1990 | Tardy et al. | |
| 4,942,875 A | 7/1990 | Hlavacek et al. | |
| 4,948,540 A | 8/1990 | Nigam | |
| 4,950,483 A | 8/1990 | Ksander et al. | |
| 4,970,298 A | 11/1990 | Silver et al. | |
| 5,002,551 A | 3/1991 | Linsky et al. | |
| 5,147,374 A | 9/1992 | Fernandez | |
| 5,162,430 A | 11/1992 | Rhee et al. | |
| 5,171,273 A | 12/1992 | Silver et al. | |
| 5,176,692 A | 1/1993 | Wilk et al. | |
| 5,192,301 A | 3/1993 | Kamiya et al. | |
| 5,196,185 A | 3/1993 | Silver et al. | |
| 5,201,745 A | 4/1993 | Tayot et al. | |
| 5,201,764 A | 4/1993 | Kelman et al. | |
| 5,206,028 A | 4/1993 | Li | |
| 5,217,493 A | 6/1993 | Raad et al. | |
| 5,254,133 A | 10/1993 | Seid | |
| 5,256,418 A | 10/1993 | Kemp et al. | |
| 5,263,983 A | 11/1993 | Yoshizato et al. | |
| 5,304,595 A | 4/1994 | Rhee et al. | |
| 5,306,500 A | 4/1994 | Rhee et al. | |
| 5,324,775 A | 6/1994 | Rhee et al. | |
| 5,328,955 A | 7/1994 | Rhee et al. | |
| 5,334,527 A | 8/1994 | Brysk | |
| 5,339,657 A | 8/1994 | Mcmurray | |
| 5,350,583 A | 9/1994 | Yoshizato et al. | |
| 5,356,432 A | 10/1994 | Rutkow et al. | |
| 5,368,549 A | 11/1994 | Mcvicker | |
| 5,376,375 A | 12/1994 | Rhee et al. | |
| 5,376,376 A | 12/1994 | Li | |
| 5,397,331 A | 3/1995 | Himpens et al. | |
| 5,399,361 A | 3/1995 | Song et al. | |
| 5,413,791 A | 5/1995 | Rhee et al. | |
| 5,425,740 A | 6/1995 | Hutchinson, Jr. | |
| 5,428,022 A | 6/1995 | Palefsky et al. | |
| 5,433,996 A | 7/1995 | Kranzler et al. | |
| 5,441,491 A | 8/1995 | Verschoor et al. | |
| 5,441,508 A | 8/1995 | Gazielly et al. | |
| 5,456,693 A | 10/1995 | Conston et al. | |
| 5,456,711 A | 10/1995 | Hudson | |
| 5,466,462 A | 11/1995 | Rosenthal et al. | |
| 5,480,644 A | 1/1996 | Freed | |
| 5,487,895 A | 1/1996 | Dapper et al. | |
| 5,490,984 A | 2/1996 | Freed | |
| 5,512,291 A | 4/1996 | Li | |
| 5,512,301 A | 4/1996 | Song et al. | |
| 5,514,181 A | 5/1996 | Light et al. | |
| 5,522,840 A | 6/1996 | Krajicek | |
| 5,523,348 A | 6/1996 | Rhee et al. | |
| 5,536,656 A | 7/1996 | Kemp et al. | |
| 5,543,441 A | 8/1996 | Rhee et al. | |
| 5,565,210 A | 10/1996 | Rosenthal et al. | |
| 5,567,806 A | 10/1996 | Abdul-Malak et al. | |
| 5,569,273 A | 10/1996 | Titone et al. | |
| RE35,399 E | 12/1996 | Eisenberg | |
| 5,593,441 A | 1/1997 | Lichtenstein et al. | |
| 5,595,621 A | 1/1997 | Light et al. | |
| 5,601,571 A | 2/1997 | Moss | |
| 5,607,474 A | 3/1997 | Athanasiou et al. | |
| 5,607,590 A | 3/1997 | Shimizu | |
| 5,614,587 A | 3/1997 | Rhee et al. | |
| 5,618,551 A | 4/1997 | Tardy et al. | |
| 5,634,931 A | 6/1997 | Kugel | |
| 5,639,796 A | 6/1997 | Lee | |
| 5,665,391 A | 9/1997 | Lea | |
| 5,667,839 A | 9/1997 | Berg | |
| 5,681,568 A | 10/1997 | Goldin et al. | |
| 5,686,115 A | 11/1997 | Vournakis et al. | |
| 5,690,675 A | 11/1997 | Sawyer et al. | |
| 5,695,525 A | 12/1997 | Mulhauser et al. | |
| 5,697,978 A | 12/1997 | Sgro | |
| 5,700,476 A | 12/1997 | Rosenthal et al. | |
| 5,700,477 A | 12/1997 | Rosenthal et al. | |
| 5,709,934 A | 1/1998 | Bell et al. | |
| 5,716,409 A | 2/1998 | Debbas | |
| 5,720,981 A | 2/1998 | Eisinger | |
| 5,732,572 A | 3/1998 | Litton | |
| 5,749,895 A | 5/1998 | Sawyer et al. | |
| 5,752,974 A | 5/1998 | Rhee et al. | |
| 5,766,246 A | 6/1998 | Mulhauser et al. | |
| 5,766,631 A | 6/1998 | Arnold | |
| 5,769,864 A | 6/1998 | Kugel | |
| 5,771,716 A | 6/1998 | Schlussel | |
| 5,785,983 A | 7/1998 | Furlan et al. | |
| 5,800,541 A | 9/1998 | Rhee et al. | |
| 5,814,328 A | 9/1998 | Gunasekaran | |
| 5,833,705 A | 11/1998 | Ken et al. | |
| 5,840,011 A | 11/1998 | Landgrebe et al. | |
| 5,861,034 A | 1/1999 | Taira et al. | |
| 5,863,984 A | 1/1999 | Doillon et al. | |
| 5,869,080 A | 2/1999 | Mcgregor et al. | |
| 5,871,767 A | 2/1999 | Dionne et al. | |
| 5,876,444 A | 3/1999 | Lai | |
| 5,891,558 A | 4/1999 | Bell et al. | |
| 5,899,909 A | 5/1999 | Claren et al. | |
| 5,906,937 A | 5/1999 | Sugiyama et al. | |
| 5,910,149 A | 6/1999 | Kuzmak | |
| 5,911,731 A | 6/1999 | Pham et al. | |
| 5,916,225 A | 6/1999 | Kugel | |
| 5,919,232 A | 7/1999 | Chaffringeon et al. | |
| 5,919,233 A | 7/1999 | Knopf et al. | |
| 5,922,026 A | 7/1999 | Chin | |
| 5,931,165 A | 8/1999 | Reich et al. | |
| 5,942,278 A | 8/1999 | Hagedorn et al. | |
| 5,962,136 A | 10/1999 | Dewez et al. | |
| 5,972,022 A | 10/1999 | Huxel | |
| RE36,370 E | 11/1999 | Li | |
| 5,993,844 A | 11/1999 | Abraham et al. | |
| 5,994,325 A | 11/1999 | Roufa et al. | |
| 5,997,895 A | 12/1999 | Narotam et al. | |
| 6,001,895 A | 12/1999 | Harvey et al. | |
| 6,008,292 A | 12/1999 | Lee et al. | |
| 6,015,844 A | 1/2000 | Harvey et al. | |
| 6,039,686 A | 3/2000 | Robert | |
| 6,042,534 A | 3/2000 | Gellman et al. | |
| 6,042,592 A | 3/2000 | Schmitt | |
| 6,043,089 A | 3/2000 | Sugiyama et al. | |
| 6,051,425 A | 4/2000 | Morota et al. | |
| 6,056,688 A | 5/2000 | Benderev et al. | |
| 6,056,970 A | 5/2000 | Greenawalt et al. | |

(56)           References Cited

U.S. PATENT DOCUMENTS

| | | | |
|---|---|---|---|
| 6,057,148 A | 5/2000 | Sugiyama et al. |
| 6,063,396 A | 5/2000 | Kelleher |
| 6,066,776 A | 5/2000 | Goodwin et al. |
| 6,066,777 A | 5/2000 | Benchetrit |
| 6,071,292 A | 6/2000 | Makower et al. |
| 6,077,281 A | 6/2000 | Das |
| 6,080,194 A | 6/2000 | Pachence et al. |
| 6,083,522 A | 7/2000 | Chu et al. |
| 6,120,539 A | 9/2000 | Eldridge et al. |
| 6,132,765 A | 10/2000 | Dicosmo et al. |
| 6,143,037 A | 11/2000 | Goldstein et al. |
| 6,153,292 A | 11/2000 | Bell et al. |
| 6,162,962 A | 12/2000 | Hinsch et al. |
| 6,165,488 A | 12/2000 | Tardy et al. |
| 6,171,318 B1 | 1/2001 | Kugel et al. |
| 6,174,320 B1 | 1/2001 | Kugel et al. |
| 6,176,863 B1 | 1/2001 | Kugel et al. |
| 6,179,872 B1 | 1/2001 | Bell et al. |
| 6,197,325 B1 | 3/2001 | Macphee et al. |
| 6,197,934 B1 | 3/2001 | Devore et al. |
| 6,197,935 B1 | 3/2001 | Doillon et al. |
| 6,210,439 B1 | 4/2001 | Firmin et al. |
| 6,221,109 B1 | 4/2001 | Geistlich et al. |
| 6,224,616 B1 | 5/2001 | Kugel |
| 6,241,768 B1 | 6/2001 | Agarwal et al. |
| 6,258,124 B1 | 7/2001 | Darois et al. |
| 6,262,332 B1 | 7/2001 | Ketharanathan |
| 6,264,702 B1 | 7/2001 | Ory et al. |
| 6,267,772 B1 | 7/2001 | Mulhauser et al. |
| 6,277,397 B1 | 8/2001 | Shimizu |
| 6,280,453 B1 | 8/2001 | Kugel et al. |
| 6,287,316 B1 | 9/2001 | Agarwal et al. |
| 6,290,708 B1 | 9/2001 | Kugel et al. |
| 6,306,424 B1 | 10/2001 | Vyakarnam et al. |
| 6,312,474 B1 | 11/2001 | Francis et al. |
| 6,328,686 B1 | 12/2001 | Robert |
| 6,334,872 B1 | 1/2002 | Termin et al. |
| 6,383,201 B1 | 5/2002 | Dong |
| 6,391,333 B1 | 5/2002 | Li et al. |
| 6,391,939 B2 | 5/2002 | Tayot et al. |
| 6,408,656 B1 | 6/2002 | Ory et al. |
| 6,410,044 B1 | 6/2002 | Chudzik et al. |
| 6,413,742 B1 | 7/2002 | Olsen et al. |
| 6,428,978 B1 | 8/2002 | Olsen et al. |
| 6,436,030 B2 | 8/2002 | Rehil |
| 6,440,167 B2 | 8/2002 | Shimizu |
| 6,443,964 B1 | 9/2002 | Ory et al. |
| 6,447,551 B1 | 9/2002 | Goldmann |
| 6,447,802 B2 | 9/2002 | Sessions et al. |
| 6,448,378 B2 | 9/2002 | Devore et al. |
| 6,451,032 B1 | 9/2002 | Ory et al. |
| 6,451,301 B1 | 9/2002 | Sessions et al. |
| 6,454,787 B1 | 9/2002 | Maddalo et al. |
| 6,477,865 B1 | 11/2002 | Matsumoto |
| 6,479,072 B1 | 11/2002 | Morgan et al. |
| 6,500,464 B2 | 12/2002 | Ceres et al. |
| 6,509,031 B1 | 1/2003 | Miller et al. |
| 6,511,958 B1 | 1/2003 | Atkinson et al. |
| 6,514,286 B1 | 2/2003 | Leatherbury et al. |
| 6,514,514 B1 | 2/2003 | Atkinson et al. |
| 6,540,773 B2 | 4/2003 | Dong |
| 6,541,023 B1 | 4/2003 | Andre et al. |
| 6,548,077 B1 | 4/2003 | Gunasekaran |
| 6,554,855 B1 | 4/2003 | Dong |
| 6,559,119 B1 | 5/2003 | Burgess et al. |
| 6,566,345 B2 | 5/2003 | Miller et al. |
| 6,575,988 B2 | 6/2003 | Rousseau |
| 6,576,019 B1 | 6/2003 | Atala |
| 6,596,002 B2 | 7/2003 | Therin et al. |
| 6,596,304 B1 | 7/2003 | Bayon et al. |
| 6,599,323 B2 | 7/2003 | Melican et al. |
| 6,599,524 B2 | 7/2003 | Li et al. |
| 6,599,690 B1 | 7/2003 | Abraham et al. |
| 6,613,348 B1 | 9/2003 | Jain |
| 6,623,963 B1 | 9/2003 | Mueller et al. |
| 6,630,414 B1 | 10/2003 | Matsumoto |
| 6,638,284 B1 | 10/2003 | Rousseau et al. |
| 6,652,594 B2 | 11/2003 | Francis et al. |
| 6,653,450 B1 | 11/2003 | Berg et al. |
| 6,656,206 B2 | 12/2003 | Corcoran et al. |
| 6,660,280 B1 | 12/2003 | Allard et al. |
| 6,669,735 B1 | 12/2003 | Pelissier |
| 6,682,760 B2 | 1/2004 | Noff et al. |
| 6,685,714 B2 | 2/2004 | Rousseau |
| 6,706,684 B1 | 3/2004 | Bayon et al. |
| 6,706,690 B2 | 3/2004 | Reich et al. |
| 6,719,795 B1 | 4/2004 | Bryan et al. |
| 6,723,335 B1 | 4/2004 | Moehlenbruck et al. |
| 6,730,299 B1 | 5/2004 | Tayot et al. |
| 6,736,823 B2 | 5/2004 | Darois et al. |
| 6,743,435 B2 | 6/2004 | Devore et al. |
| 6,755,868 B2 | 6/2004 | Rousseau |
| 6,773,723 B1 | 8/2004 | Spiro et al. |
| 6,783,554 B2 | 8/2004 | Amara et al. |
| 6,790,213 B2 | 9/2004 | Cherok et al. |
| 6,790,454 B1 | 9/2004 | Abdul et al. |
| 6,800,082 B2 | 10/2004 | Rousseau |
| 6,833,408 B2 | 12/2004 | Sehl et al. |
| 6,835,336 B2 | 12/2004 | Watt |
| 6,852,330 B2 | 2/2005 | Bowman et al. |
| 6,869,938 B1 | 3/2005 | Schwartz et al. |
| 6,893,653 B2 | 5/2005 | Abraham et al. |
| 6,896,904 B2 | 5/2005 | Spiro et al. |
| 6,936,276 B2 | 8/2005 | Spiro et al. |
| 6,939,562 B2 | 9/2005 | Spiro et al. |
| 6,949,625 B2 | 9/2005 | Tayot |
| 6,966,918 B1 | 11/2005 | Schuldt-Hempe et al. |
| 6,971,252 B2 | 12/2005 | Therin et al. |
| 6,974,679 B2 | 12/2005 | Andre et al. |
| 6,974,862 B2 | 12/2005 | Ringeisen et al. |
| 6,977,231 B1 | 12/2005 | Matsuda |
| 6,988,386 B1 | 1/2006 | Okawa et al. |
| 7,025,063 B2 | 4/2006 | Snitkin et al. |
| 7,041,868 B2 | 5/2006 | Greene et al. |
| RE39,172 E | 7/2006 | Bayon et al. |
| 7,098,315 B2 | 8/2006 | Schaufler |
| 7,101,381 B2 | 9/2006 | Ford et al. |
| 7,115,220 B2 | 10/2006 | Dubson et al. |
| 7,156,858 B2 | 1/2007 | Schuldt-Hempe et al. |
| 7,175,852 B2 | 2/2007 | Simmoteit et al. |
| 7,192,604 B2 | 3/2007 | Brown et al. |
| 7,207,962 B2 | 4/2007 | Anand et al. |
| 7,214,765 B2 | 5/2007 | Ringeisen et al. |
| 7,226,611 B2 | 6/2007 | Yura et al. |
| 7,229,453 B2 | 6/2007 | Anderson et al. |
| 7,331,199 B2 | 2/2008 | Ory et al. |
| 7,594,921 B2 | 9/2009 | Browning |
| 7,615,065 B2 | 11/2009 | Priewe et al. |
| 7,670,380 B2 | 3/2010 | Cauthen, III |
| 7,709,017 B2 | 5/2010 | Tayot et al. |
| 7,713,463 B1 | 5/2010 | Reah et al. |
| 7,718,556 B2 | 5/2010 | Matsuda et al. |
| 7,732,354 B2 | 6/2010 | Fricke et al. |
| 7,785,334 B2 | 8/2010 | Ford et al. |
| 7,799,767 B2 | 9/2010 | Lamberti et al. |
| 7,806,905 B2 | 10/2010 | Ford et al. |
| 7,824,420 B2 | 11/2010 | Eldridge et al. |
| 7,846,171 B2 | 12/2010 | Kullas et al. |
| 7,905,825 B2 | 3/2011 | Amal et al. |
| 7,942,104 B2 | 5/2011 | Butcher et al. |
| 7,946,236 B2 | 5/2011 | Butcher |
| 8,074,591 B2 | 12/2011 | Butcher et al. |
| 8,142,515 B2 | 3/2012 | Therin et al. |
| 8,197,837 B2 | 6/2012 | Jamiolkowski et al. |
| 8,323,675 B2 | 12/2012 | Greenawalt |
| 8,366,787 B2 | 2/2013 | Brown et al. |
| 8,418,508 B2 | 4/2013 | Lecuivre et al. |
| 8,709,094 B2 | 4/2014 | Stad et al. |
| 8,834,578 B2 | 9/2014 | Bayon et al. |
| 8,834,864 B2 | 9/2014 | Odar et al. |
| 8,846,060 B2 | 9/2014 | Archibald et al. |
| 8,877,233 B2 | 11/2014 | Obermiller et al. |
| 8,888,863 B2 | 11/2014 | Walther et al. |
| 8,956,373 B2 | 2/2015 | Ford et al. |

(56) References Cited

U.S. PATENT DOCUMENTS

| | | | |
|---|---|---|---|
| 8,961,850 B2 | 2/2015 | Wood et al. | |
| 9,034,357 B2 | 5/2015 | Stopek | |
| 9,186,235 B2 | 11/2015 | Ory et al. | |
| 9,398,943 B2 | 7/2016 | Criscuolo et al. | |
| 9,445,883 B2 | 9/2016 | Ecuivre et al. | |
| 9,820,843 B2 | 11/2017 | Greenhalgh et al. | |
| 10,787,757 B2* | 9/2020 | Rudolph | D05B 69/18 |
| 2002/0095218 A1 | 7/2002 | Carr et al. | |
| 2003/0086975 A1 | 5/2003 | Ringeisen | |
| 2003/0114937 A1 | 6/2003 | Leatherbury et al. | |
| 2003/0133967 A1 | 7/2003 | Ruszczak et al. | |
| 2003/0225355 A1 | 12/2003 | Butler | |
| 2004/0024403 A1* | 2/2004 | Ellis | A61B 17/7055 |
| | | | 606/60 |
| 2004/0034373 A1 | 2/2004 | Schuldt-Hempe et al. | |
| 2004/0059356 A1 | 3/2004 | Gingras | |
| 2004/0078089 A1 | 4/2004 | Ellis et al. | |
| 2004/0101546 A1 | 5/2004 | Gorman et al. | |
| 2004/0172048 A1* | 9/2004 | Browning | A61F 2/0063 |
| | | | 606/151 |
| 2005/0002893 A1 | 1/2005 | Goldmann | |
| 2005/0021058 A1 | 1/2005 | Negro | |
| 2005/0048859 A1* | 3/2005 | Canham | D01F 1/10 |
| | | | 442/415 |
| 2005/0085924 A1 | 4/2005 | Darois et al. | |
| 2005/0113849 A1 | 5/2005 | Popadiuk et al. | |
| 2005/0137512 A1 | 6/2005 | Campbell et al. | |
| 2005/0142161 A1 | 6/2005 | Freeman et al. | |
| 2005/0148963 A1 | 7/2005 | Brennan | |
| 2005/0175659 A1 | 8/2005 | Macomber et al. | |
| 2005/0232979 A1 | 10/2005 | Shoshan | |
| 2005/0267521 A1 | 12/2005 | Forsberg | |
| 2005/0288691 A1 | 12/2005 | Leiboff | |
| 2006/0135921 A1 | 6/2006 | Wiercinski et al. | |
| 2006/0147501 A1 | 7/2006 | Hillas et al. | |
| 2006/0216320 A1 | 9/2006 | Kitazono et al. | |
| 2006/0229596 A1* | 10/2006 | Weiser | A61B 17/0401 |
| | | | 606/37 |
| 2006/0252981 A1 | 11/2006 | Matsuda et al. | |
| 2007/0299538 A1 | 12/2007 | Roeber | |
| 2008/0173223 A1 | 7/2008 | Butcher et al. | |
| 2008/0178786 A1 | 7/2008 | Butcher | |
| 2009/0011507 A1* | 1/2009 | Ellis | A61L 27/50 |
| | | | 435/395 |
| 2009/0138082 A1 | 5/2009 | Reah et al. | |
| 2009/0192532 A1 | 7/2009 | Spinnler et al. | |
| 2010/0089297 A1* | 4/2010 | Butcher | D05C 7/00 |
| | | | 112/440 |
| 2010/0189764 A1* | 7/2010 | Thomas | A61P 43/00 |
| | | | 514/6.9 |
| 2012/0150204 A1 | 6/2012 | Mortarino et al. | |
| 2013/0172915 A1 | 7/2013 | Thomas et al. | |
| 2018/0168791 A1* | 6/2018 | Gorman | A61F 2/0063 |
| 2018/0271505 A1 | 9/2018 | Quintero et al. | |
| 2018/0303592 A1 | 10/2018 | Taylor et al. | |

FOREIGN PATENT DOCUMENTS

| | | | |
|---|---|---|---|
| DE | 10019604 A1 | 10/2001 | |
| DE | 10043396 C1 | 6/2002 | |
| EP | 0194192 A1 | 9/1986 | |
| EP | 0248544 A1 | 12/1987 | |
| EP | 0276890 A2 | 8/1988 | |
| EP | 0372969 A1 | 6/1990 | |
| EP | 0544485 A1 | 6/1993 | |
| EP | 0552576 A1 | 7/1993 | |
| EP | 0614650 A2 | 9/1994 | |
| EP | 0621014 A1 | 10/1994 | |
| EP | 0625891 A1 | 11/1994 | |
| EP | 0637452 A1 | 2/1995 | |
| EP | 0705878 A2 | 4/1996 | |
| EP | 0719527 A1 | 7/1996 | |
| EP | 0774240 A1 | 5/1997 | |
| EP | 0797962 A2 | 10/1997 | |
| EP | 0827724 A2 | 3/1998 | |
| EP | 0836838 A1 | 4/1998 | |
| EP | 0895762 A2 | 2/1999 | |
| EP | 0898944 A2 | 3/1999 | |
| EP | 1017415 A1 | 7/2000 | |
| EP | 1052319 A1 | 11/2000 | |
| EP | 1055757 A1 | 11/2000 | |
| EP | 1216717 A1 | 6/2002 | |
| EP | 1216718 A1 | 6/2002 | |
| EP | 0693523 B1 | 11/2002 | |
| EP | 1315468 A2 | 6/2003 | |
| EP | 1382728 A1 | 1/2004 | |
| EP | 1484070 A1 | 12/2004 | |
| EP | 1561480 A2 | 8/2005 | |
| EP | 1782848 A2 | 5/2007 | |
| EP | 2514862 A2 | 10/2012 | |
| ES | 2540597 A1 | 7/2015 | |
| FR | 2244853 A1 | 4/1975 | |
| FR | 2257262 A1 | 8/1975 | |
| FR | 2308349 A1 | 11/1976 | |
| FR | 2453231 A1 | 10/1980 | |
| FR | 2715405 A1 | 7/1995 | |
| FR | 2724563 A1 | 3/1996 | |
| FR | 2744906 A1 | 8/1997 | |
| FR | 2766698 A1 | 2/1999 | |
| FR | 2771622 A1 | 6/1999 | |
| FR | 2779937 A1 | 12/1999 | |
| FR | 2859624 B1 | 12/2005 | |
| FR | 2863277 B1 | 6/2006 | |
| FR | 2884706 B1 | 4/2008 | |
| GB | 2051153 A | 1/1981 | |
| JP | H0332677 U | 3/1991 | |
| JP | H05237128 A | 9/1993 | |
| JP | H09137380 A | 5/1997 | |
| JP | 2004510543 A | 4/2004 | |
| JP | 2010005417 A | 1/2010 | |
| JP | 2014523325 A | 9/2014 | |
| WO | 8902445 A1 | 3/1989 | |
| WO | 8908467 A1 | 9/1989 | |
| WO | 9012551 A1 | 11/1990 | |
| WO | 9206639 A2 | 4/1992 | |
| WO | 9220349 A1 | 11/1992 | |
| WO | 9311805 A1 | 6/1993 | |
| WO | 9318174 A1 | 9/1993 | |
| WO | 9417747 A1 | 8/1994 | |
| WO | 9507666 A1 | 3/1995 | |
| WO | 9518638 A1 | 7/1995 | |
| WO | 9532687 A1 | 12/1995 | |
| WO | 9603091 A1 | 2/1996 | |
| WO | 9608277 A1 | 3/1996 | |
| WO | 9609795 A1 | 4/1996 | |
| WO | 9614805 A1 | 5/1996 | |
| WO | 9641588 A1 | 12/1996 | |
| WO | 9735533 A1 | 10/1997 | |
| WO | 9835632 A1 | 8/1998 | |
| WO | 9849967 A1 | 11/1998 | |
| WO | 9905990 A1 | 2/1999 | |
| WO | 9906079 A1 | 2/1999 | |
| WO | 9906080 A1 | 2/1999 | |
| WO | 9951163 A1 | 10/1999 | |
| WO | 0016821 A1 | 3/2000 | |
| WO | 0067663 A1 | 11/2000 | |
| WO | 0115625 A1 | 3/2001 | |
| WO | 0180773 A1 | 11/2001 | |
| WO | 0181667 A1 | 11/2001 | |
| WO | 0207648 A1 | 1/2002 | |
| WO | 02078568 A1 | 10/2002 | |
| WO | 03002168 A1 | 1/2003 | |
| WO | 2004004600 A1 | 1/2004 | |
| WO | 2004071349 A2 | 8/2004 | |
| WO | 2004078120 A2 | 9/2004 | |
| WO | 2004103212 A1 | 12/2004 | |
| WO | 2005011280 A1 | 2/2005 | |
| WO | 2005013863 A2 | 2/2005 | |
| WO | 2005018698 A1 | 3/2005 | |
| WO | 2005105172 A1 | 11/2005 | |
| WO | 2006018552 A1 | 2/2006 | |
| WO | 2006023444 A2 | 3/2006 | |
| WO | 2008075398 A2 | 6/2008 | |

(56)  References Cited

FOREIGN PATENT DOCUMENTS

| WO | 2009071998 A2 | 6/2009 |
| WO | 2009031035 A3 | 1/2010 |
| WO | 2007048099 A3 | 9/2010 |
| WO | 2011027087 A1 | 3/2011 |
| WO | 2017214620 A1 | 12/2017 |
| WO | 2018135568 A1 | 7/2018 |

OTHER PUBLICATIONS

Notice of Allowance issued in Japanese Patent Application No. 2019-200758 dated Aug. 5, 2024 with English translation.
European Search Report for EP 18206825.4 date of completion is Sep. 4, 2019 (6 pages).
Japanese Office Action issued in Japanese Patent Application No. 2019-200758 dated Mar. 11, 2024 with English translation.

\* cited by examiner

600

601

690

607

605

610
610
610
620
691

METHODS OF FORMING IMPLANTS SUITABLE FOR SOFT TISSUE REPAIR

CROSS-REFERENCE TO RELATED APPLICATIONS

This application is a divisional application of U.S. patent application Ser. No. 16/666,551 filed Oct. 29, 2019, which claims benefit of and priority to European Patent Application Serial No. 18206825.4 filed Nov. 16, 2018, the disclosure of each of the above-identified applications is hereby incorporated by reference in its entirety.

TECHNICAL FIELD

The present disclosure relates generally to implants suitable for soft tissue repair, such as hernia or prolapse repair, the implants include an implantable web including a combination of laid yarns and threading yarns and optionally a substrate.

BACKGROUND

Conventional surgical meshes have been used during both laparoscopic and open surgery for the treatment of many types of hernias and/or prolapse.

During the surgical treatment of a hernia or prolapse, the opening of the defect in the tissue may be closed and bridged with a conventional surgical mesh, such as a knitted, braided, and/or woven mesh. In conventional surgical mesh, the yarns forming the overall structure of the mesh are often knitted, braided and/or woven together tightly and locked into place with each other. For example, a knit mesh commonly includes yarns knitted together in at least a warp and weft direction such that the warp and weft yarns are tightly interwoven with each other to ensure the warp and weft yarns are locked into a position relative to each other to form and maintain the overall structure of the knit mesh. The tighter the yarns are interwoven, the stiffer and/or less adaptable a mesh becomes.

Conventional mesh which are stiff and less adaptable: are more likely to irritate the wound when stressed, which may result in increased post-operative pain and discomfort for a patient; and/or, may be less likely to quickly adapt the muscular contractions and sudden changes in mechanical behavior of abdominal wall tissue during patient activities, which may result in mechanical failure of the mesh, failure of the mesh to maintain reinforcement function, and/or recurrence of the hernia or prolapse.

It would be an object of the present application to provide implants which are more elastic than conventional mesh. Specifically, the implants described herein are capable of returning to their original configuration after being stressed, without having been damaged, i.e., permanently deformed. The implants are also more adaptable to contractions and/or abdominal wall motion of a patient.

It would further be an object of the present application to provide implants configured to adapt to the unidirectional stresses associated with day-to-day patient activities (such as sitting, breathing, laying down, standing up, etc.) without irritating the wound and/or inflicting additional pain or discomfort to patient post-surgery.

It would further be an object of the present application to provide implants configured to adapt to the multidirectional stresses associated sometimes with increased patient activities (such as exercising, running, jumping, etc.) by stretching multiaxially (without failing, permanently deforming, and/ or bulging) while maintaining the ability to return to the implants original configuration so as to maintain reinforcement function.

It would further be an object of the present application to provide implants configured to distribute stress efficiently and/or evenly throughout the implant, so in the event of local failure of only a portion of the implant, the implant can still maintain reinforcement function.

Each of these may improve the outcomes of hernia or prolapse repair, either structurally and/or symptomatically.

SUMMARY

The present disclosure describes implants for hernia and/or prolapse repair including an implantable web and optionally a substrate. The implantable web includes a plurality of laid yarns and a plurality of threading yarns. The plurality of laid yarns overlap or crisscross each other and are not interwoven. The laid yarns may be selected from axial yarns, radial yarns, spiral yarns, framing yarns, mooring yarns, vertical yarns, horizontal yarns, diagonal yarns, and reinforcing yarns. The plurality of threading yarns may include at least a first and second threading yarn. The threading yarns interlace each other along the length of the laid yarns to form locking stitches around any combination of the laid yarns, and in particular at least two of the laid yarns, thereby holding the laid yarns into position relative to each other to form and/or maintain the structure of the web.

In some embodiments, the webs described herein may be formed from a plurality of laid yarns and a plurality of threading yarns, the laid yarns include at least a plurality of radial yarns and a plurality of spiral yarns and the threading yarns include at least first and second threading yarns. In such embodiments, the webs may further include a central aperture free of any yarns. In some embodiments, the webs may further include at least one of a substrate, a framing yarn, a mooring yarn, a vertical yarn, horizontal yarn, diagonal yarn, a reinforcing yarn, or a suture assembly.

In some embodiments, the webs described herein may be formed from a plurality of laid yarns and a plurality of threading yarns, the laid yarns include at least one axial yarn, a plurality of radial yarns, and a plurality of spiral yarns and the threading yarns include at least first and second threading yarns. In some embodiments, the webs may further include at least one of a substrate, a framing yarn, a mooring yarn, a vertical yarn, horizontal yarn, diagonal yarn, a reinforcing yarn, or a suture assembly.

In some embodiments in which the webs include a substrate, the substrate may be a dissolvable sheet or textile. In some embodiments, the substrate is a knit textile.

In some embodiments in which the webs include at least one framing yarn, the framing yarn may define a perimeter of the outer edge of the web in shape different than the shape of the spiral yarns.

In some embodiments in which the webs include at least one mooring yarn, the mooring yarn may extend radially from the framing yarn.

In some embodiments in which the webs include at least one reinforcing yarn, the reinforcing yarn may be configured to form a reinforcement member or zone. The reinforcement member or zone may be a continuous or discontinuous ring.

In some embodiments in which the webs include at least one suture assembly, the suture assembly may be centered on a face of the web.

In some embodiments, at least one of the radial yarns, vertical yarns, horizontal yarns, or diagonal yarns may form at least one radial loop, vertical loop, horizontal loop, or diagonal loop, respectively, beyond an outer edge of the web.

In some embodiments, the implants include at least one implantable web, the web including a plurality of laid yarns and a plurality of threading yarns. The plurality of laid yarns include a plurality of radial yarns, each radial yarn extending in a radial direction from a central area of the web to an outer peripheral edge of the web, and a plurality of spiral yarns, each spiral yarn forming a continuous loop around the central area of the web and extending between and criss-crossing over the plurality of radial yarns, wherein the central area of the web is a central aperture free of any of the laid and threading yarns. The plurality of threading yarns include at least a first and a second threading yarn, wherein the first and second threading yarns are interwoven to each other to form a locking stitches, the locking stitches positioned around at least the radial yarns and the spiral yarns to hold the radial yarns and spiral yarns in a position relative to each other to maintain the overall structure of the web.

In some embodiments, the implants include at least one implantable web, the web including a plurality of laid yarns and a plurality of threading yarns. The plurality of laid yarns including at least one axial yarn, at least one spiral yarn, and a plurality of radial yarns, the axial yarn extending along a portion of a central axis of at least one face of the web, each radial yarn extending in a radial direction from the axial yarn to an outer peripheral edge of the web, and the at least one spiral yarn forming a loop around the axial yarn and extending between and crisscrossing over the plurality of radial yarns. The plurality of threading yarns include at least a first and a second threading yarn, wherein the first and second threading yarns are interwoven to each other to form locking stitches, the locking stitches positioned around any combination of the axial yarn, the radial yarns, and the spiral yarns to hold the axial yarn, the radial yarns, and spiral yarns in a position relative to each other to maintain the overall structure of the web.

DESCRIPTION OF THE DRAWINGS

Various embodiments of the presently disclosed barbed filaments are disclosed herein with reference to the drawings, wherein.

DETAILED DESCRIPTION

Figure 1A:
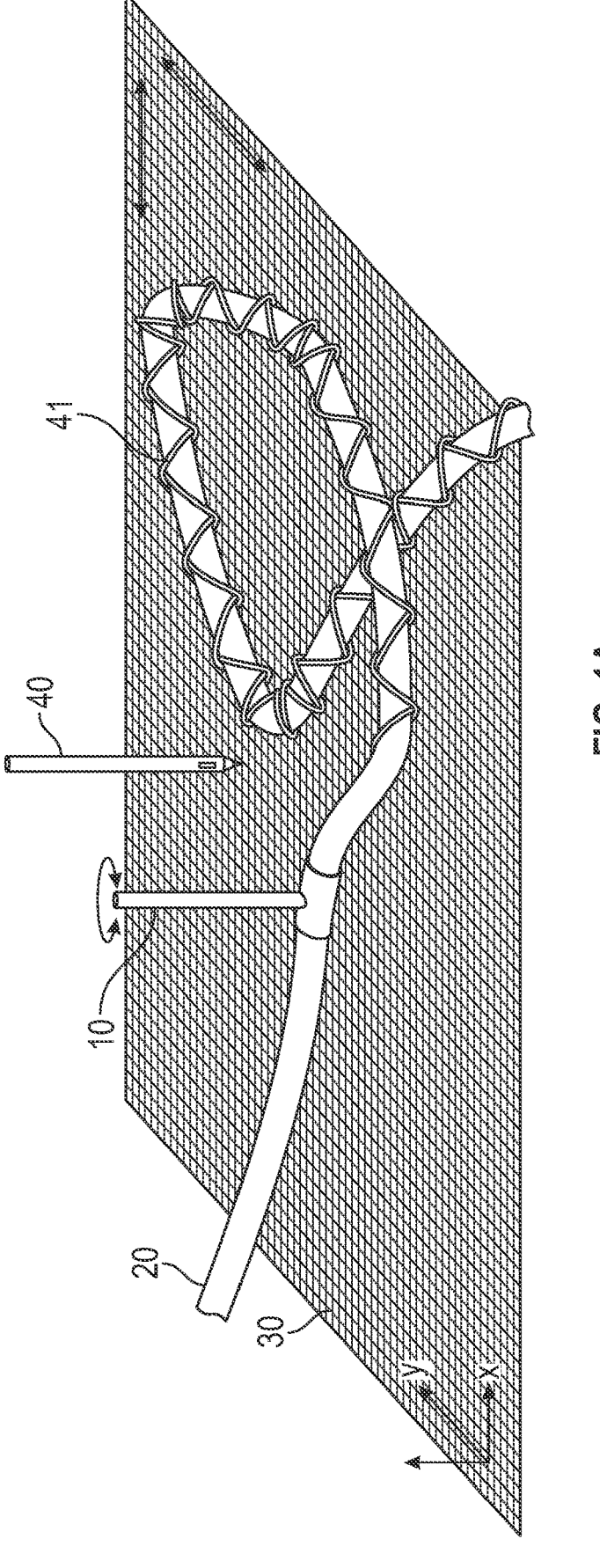
FIGS. 1A and 1B are perspective and side schematic views, respectively, of a process used to form a surgical implant including a web as described in at least one embodiment herein.

As illustrated in many of the figures herein, the implants described herein are generally planar and include at least an implantable web and optionally a substrate attached thereto. In addition, the implants may further include a suture assembly, a reinforcement member, or both.

The implants are configured to be surgically implanted into tissue to reinforce and/or support the closure of an opening in soft tissue, such as in hernia or prolapse repair procedures. In some embodiments, the implants are configured to repair a hernia, such as an inguinal hernia, femoral hernia, umbilical hernia, incisional hernia, ventral hernia, parastomal hernia, and the like. In some embodiments, the implants are configured to repair prolapse of the rectum, bladder, uterus, or vagina.

I. Implantable Webs

The implants described herein include at least one implantable web, the web including at least a first and second face opposite each other with a thickness therebetween. The implantable webs are defined by an outer peripheral edge, the outer peripheral edge being of any shape, such as rectangular, circular, elliptical, triangular, rectangular, pentagonal, hexagonal, octagonal, etc. The web, like the overall implant, is generally planar.

The implantable webs are formed from a combination of laid yarns and threading yarns. The laid yarns are positioned or laid in an overlapping or crisscrossing manner which is free-flowing. The laid yarns are not interwoven with each other. The threading yarns form locking stitches around the individual laid yarns at or near the site of overlap of the laid yarns to lock the laid yarns into a generally fixed position relative to each other to form and/or maintain the overall structure the implantable web.

In some embodiments, the implants may further include a substrate on which the laid yarns and the threading yarns may be combined. Any substrate combined with the various yarns can either remain part of the implant (or implantable web) after manufacture or be removed from the implant (or implantable web) in part or in whole anytime thereafter.

1. Laid Yarns

Laid yarns are yarns that can be positioned or laid in an overlapping or crisscrossing manner relative to each other without being interwoven and/or held into any permanent position relative to each other (without the addition of the threading yarns). Unlike stiff conventional surgical mesh (knits, braids, weaves, etc.) which include interwoven yarns that lock each other into a fixed position relative to each other, e.g., knit textiles including warp and weft threading, the laid yarns of the present disclosure are simply free-flowing and merely overlap and/or crisscross each other without anchoring each other into a fixed position. Since the laid yarns alone are not held in any permanent position relative to each other, the laid yarns alone cannot form and/or maintain the structure of an implantable web. As described in more detail herein, the laid yarns are held or locked into an overlapping or crisscrossing position relative to each other by the addition of the threading yarns to the web.

Various types of laid yarns can be combined with the threading yarns to form the implantable webs described herein. The various types of laid yarns include axial yarns, radial yarns, spiral yarns, framing yarns, mooring yarns, vertical yarns, horizontal yarns, diagonal yarns, and reinforcing yarns.

The various laid yarns may be monofilament structures, multifilament structures, or any combination of monofilament and multifilament structures.

The various laid yarns may be made of any biocompatible material suitable for implantation. In some embodiments, the laid yarns may be formed from any combination of bioabsorbable, non-bioabsorbable, elastic, and/or non-elastic material.

Some non-limiting examples of bioabsorbable materials suitable for forming at least some of the laid yarns include polylactic acid, polyglycolic acid, polycaprolactone, polydioxanone, trimethylene carbonate, polyvinyl alcohol, polyhydroxyalkanoates, polyphosphazene, absorbable polyamides, polyethers, oxidized cellulose, chitosan, gelatin, collagen, and combinations thereof.

Some non-limiting examples of non-bioabsorbable materials suitable for forming at least some of the laid yarns include polyethylene terephthalate, non-absorbable polyamides, aramids, expanded polytetrafluroethylene, polyurethane, polyvinylidene difluoride, polybutyl esters, polyether ether ketones, polyolefins (such as polyethylene or polypropylene), copper alloys, silver alloys, platinum, gold, stainless steel, and combinations thereof.

In some embodiments, at least some of the laid yarns may be made from an elastic material. Yarns made from elastic materials, i.e., elastic yarns, display an elongation at break equal to or greater than 75% measured according to NF EN ISO 13934-1: 2013. Some non-limiting examples of elastic materials include polyurethane, polybutylene, and thermoplastic elastomers (TPE) such as styrenic block copolymers, polyolefinelastomers, and polyamides. In some embodiments, the webs described herein include elastic yarns made from a combination of polytetrahydrofurane and polybutylene.

In some embodiments, at least some of the laid yarns may be made from a non-elastic material. Yarns made from non-elastic materials, i.e., non-elastic yarns, display an elongation at break less than 75%. measured according to NF EN ISO 13934-1: 2013. Some non-limiting examples of non-elastic materials include polyethylene terephthalate, polypropylene, nickel, titanium, and other metals.

The various laid yarns are provided in more detail below.

a. Axial Yarns

The implantable webs described herein may include at least one axial yarn. An axial yarn, as illustrated in some of the figures herein, is a yarn that extends along a central axis of the implantable webs. The central axis of the web can run in a longitudinal direction along a length of the web or in a transverse direction along a width of the web. The axial yarn is centered on at least one face of the web in either a longitudinal direction or transverse direction. In some embodiments, the webs described herein include two axial yarns laid perpendicular to each other, the first axial yarn laid in the longitudinal direction and the second yarn laid in the transverse direction.

In some embodiments, an axial yarn may extend to the outer peripheral edge of the web. In some embodiments, an axial yarn may not extend to the outer peripheral edge of the webs and/or is free of the outer peripheral edge of the webs.

In some embodiments, at least one axial yarn may extend along a central longitudinal axis (CLA) of at least one face of the implantable webs. The CLA extends the length of at least one face of the web and across the center and/or central area of the web. In such embodiments, the axial yarn extends an axial distance along the CLA. The axial distance may range from about 0% to about 100% of the length of the webs. In some embodiments, the axial distance may range: from about 10% to about 90% of the length of the webs; about 25% to about 75% of the length of the webs; from about 33% to about 67% of the length of the webs; and/or from about 40% to about 60% of the length of the webs. In some embodiments, the axial distance may represent: greater than 50% of the length of the webs; about 50% of the length of the webs; or, less than 50% of the length of the webs.

In some embodiments, at least one axial yarn may extend along a central traverse axis (CTA) of at least one face of the implantable webs. The CTA extends the width of at least one face of the web and across the center and/or central area of the web. The CLA and the CTA intersect at the center and/or central area of at least one face of the web and are perpendicular to each other. In some embodiments, the axial yarn may extend an axial distance along a central traverse axis. The axial distance may range from about 0% to about 100% of the width of the webs. In some embodiments, the axial distance may range: from about 10% to about 90% of the width of the webs; from about 25% to about 75% of the width of the webs; from about 33% to about 67% of the width of the webs; or, from about 40% to about 60% of the width of the webs. In some embodiments, the axial distance may represent: greater than 50% of the width of the webs; about 50% of the width of the webs; or, less than 50% of the width of the webs.

b. Radial Yarns

The implantable webs described herein include a plurality of radial yarns. Radial yarns extend in a radial direction from a central area to an outer peripheral edge of at least one face of the web. The distance between the neighboring radial yarns on the face of the web increases, as the neighboring radial yarns extend away from the central area of the web. Individual radial yarns do not cross over other individual radial yarns. Neighboring radial yarns are not parallel to each other.

In some embodiments, the radial yarns extend from a center of at least one face of the webs. In some embodiments, the radial yarns extend from a central area around the center of the webs, wherein the center of the web is free of any yarns, i.e., a central aperture. In some embodiments, the radial yarns extend from at least one axial yarn extending along the central axis and positioned within the central area of the web.

In some embodiments, a radial yarn may extend away from the central area or center of at least one face, if not both, of the web towards an outer edge of the web as a single yarn.

In some embodiments, a radial yarn may extend away from the central area, the center, or the axial yarn of the web and beyond the outer edge of the web, which may be defined by the outermost spiral yarn, and curls back towards the central area or center of the face of the web. In such embodiments, the radial yarn crosses over the outer edge of the web or the outermost spiral yarn twice to form a radial loop therebetween. Like mooring yarns, the radial loops are suitable for anchoring the webs into tissue and may extend any distance beyond the outer edge or outermost spiral yarn.

In some embodiments, the webs described herein may include radial yarns which all form radial loops. In some embodiments, the webs described herein may include only radial yarns which do not form radial loops. In some embodiments, the webs described herein may include both radial yarns which do not form radial loops and radial yarns that do form radial loops.

In some embodiments, the implantable webs described herein include at least one axial yarn and a plurality of radial yarns. In such embodiments, the axial yarn is located in a central area, i.e., along a central longitudinal axis and/or a central traverse axis, of at least one face of the webs and the radial yarns extend from some portion of the axial yarn. In some embodiments, the radial yarns may extend from the same portion of the axial yarn. In some embodiments, the radial yarns may extend from different portions of the axial yarn. In some embodiments, the radial yarns may be equally spaced about the axial yarn. In some embodiments, the radial yarns may extend symmetrically from each side of the axial yarn. In some embodiments, the radial yarns may extend from at least one of ends, if not both ends, of the axial yarn.

c. Spiral Yarns

The implantable webs described herein further include at least one spiral yarn and may include a plurality of spiral yarns. Spiral yarns turn around the central area (including at least one of the center, a central aperture, and/or the at least one axial yarn) on at least one face, if not both, of the web.

In some embodiments, the at least one spiral yarn does not traverse the central area of at least one face, if not both, of the web. In some embodiments, the central area of at least one face, if not both, of the web described herein is free of spiral yarns.

In some embodiments, at least one the spiral yarn may start at the central area (including at least one of the center, a central aperture, and/or the at least one axial yarn) of at least one face and spiral outwardly from therefrom towards the outer perimeter edge of the web.

Spiral yarns also extend between the radial yarns thereby connecting neighboring radial yarns to each other via the spiral yarn. Alternatively, the radial yarns extend between the spiral yarns thereby connecting neighboring spiral yarns to each other via the radial yarn. The spiral yarns overlap or crisscross the radial yarns in a free-flowing manner and are not interwoven. Spiral yarns do not cross over other spiral yarns.

In some embodiments, the web may include a single continuous spiral yarn which winds from or near the outer peripheral edge of the web towards or near the central area of the web, in a continuous and gradually tightening curve around the central area of at least one face, if not both, of the web.

In some embodiments, the web may include a plurality of spiral yarns, each spiral yarn forming a closed loop around the center or central area of the web, without passing through the axial yarn and/or the central area of the web. By closed loop, the spiral yarns are not intended to be limited to only round shapes but rather are intended to include any closed shape including circular, elliptical, rectangular, triangular, hexagonal, pentagonal, etc.

Each closed loop spiral yarn is spaced a radial distance from neighboring spiral yarns. In some embodiments, the radial distance between neighboring spiral yarns remains constant throughout the web. By the radial distance remaining constant, the loops of spiral yarns around the central area of the web are equally spaced from each other on at least one face of the web.

In some embodiments, the spiral yarns are concentric around the axial yarn and/or central area of the web.

In some embodiments, the radial distance between neighboring spiral yarns increases as the spiral yarns get further away from the axial yarn and/or central area of the web. For example, the outer most neighboring spiral yarns (the two spiral yarns furthest from the central area of web) may be spaced the greatest radial distance as compared to the inner most neighboring spiral yarns (the two spiral closest to the central area of the web) being spaced the least radial distance.

In some embodiments, the radial distance between neighboring spiral yarns decreases as the spiral yarns get further from the axial yarn and/or central area of the web. For example, the outer most neighboring spiral yarns (the two spiral yarns furthest from central area of web) may be spaced the smallest radial distance as compared to the inner most neighboring spiral yarns (the two spiral yarns closest from central area of web) being spaced the greatest radial distance.

In still other embodiments, the radial distance between neighboring spiral yarns varies throughout the face of the web.

In some embodiments, the spiral yarns are non-elastic yarns.

In some embodiments, the spiral yarns are non-elastic yarns and at least one of the radial and axial yarns are elastic yarns.

In some embodiments, the implantable webs described herein include a plurality of radial yarns, a plurality of spiral yarns, and a plurality of threading yarns. In such embodiments, the plurality of radial yarns extend from a central aperture of the web to the outer peripheral edge of the web, the plurality of spiral yarns turn around the central aperture of the web forming a continuous loop and extending between the radial yarns thereby connecting neighboring radial yarns to each other via the spiral yarns. The threading yarns being interlaced to each other to form locking stitches around the radial yarns and/or spiral yarns adjacent to the location wherein the spiral yarns and radial yarns overlap and/or crisscross.

In some embodiments, the implantable webs described herein include at least one axial yarn, a plurality of radial yarns, a plurality of spiral yarns, and a plurality of threading yarns. In such embodiments, the axial yarn is located in a central area, i.e., along a central longitudinal or traverse axis, of at least one face of the web, the plurality of radial yarns extend from some portion of the axial yarn to the outer peripheral edge of the web, and the plurality of spiral yarns turn around the axial yarn and extend between the radial yarns thereby connecting neighboring radial yarns to each other via the spiral yarn. In such embodiments, the outermost spiral yarn from the axial yarn of the web may represent the outer peripheral edge of the web and the plurality of radial yarns may extend to the outermost spiral yarn. The threading yarns being interlaced to each other to form locking stitches around the axial yarn, radial yarns and/or spiral yarns adjacent to the location wherein the axial yarns, radial yarns, and/or spiral yarns overlap and/or crisscross.

d. Framing Yarns

The implantable webs described herein may further include at least one framing yarn. Framing yarns surround or enclose any combination of axial yarns, radial yarns, and/or spiral yarns to define the outer peripheral edge of the web and to provide additional support to the webs. Framing yarns overlap or crisscross a portion of the radial yarns that extends radially beyond the outermost spiral yarn. Framing yarns do not overlap or crisscross the axial yarns and/or the spiral yarns. Framing yarns do not traverse the central area of at least one face, if not both, of the web. The central area of at least one face, if not both, of the web described herein is free of framing yarns. The central area of at least one face, if not both, of the web described herein is free of framing yarns and spiral yarns.

In some embodiments, the radial yarns of the webs may extend beyond the outermost spiral yarn to framing yarns, wherein the framing yarns are displaced a radial framing distance from the outermost spiral yarn (in a direction further away from the axial yarn and/or central area of the web). In such embodiments, the radial framing distance between the outermost spiral yarn and the framing yarn may be greater than the radial distance between at least some, if not all, of the spiral yarns. In such embodiments, the radial framing distance between the outermost spiral yarn and the framing yarns creates a zone including only radial yarns and optionally threading yarns.

The framing yarns are capable of defining any shape, such as rectangular, circular, elliptical, triangular, rectangular, pentagonal, hexagonal, octagonal, etc. In some embodiments, the shape defined by the framing yarns is different than the shape defined by the spiral yarns and/or specifically, the outermost spiral yarn. In some embodiments, the framing yarns define a rectangular shape and the spiral yarns define a circular or elliptical shape.

e. Mooring Yarns

The implantable webs described herein may further include at least one mooring yarn for anchoring the webs into tissue. Mooring yarns extend from the framing yarns and away from the axial yarn and/or central area of the web. Mooring yarns overlap or crisscross a portion of the framing yarns. Mooring yarns do not overlap or crisscross the axial yarns, the radial yarns, and/or the spiral yarns. Mooring yarns do not traverse the central area of at least one face, if not both, of the web. The central area of at least one face, if not both, of the web described herein is free of mooring yarns. The central area of at least one face, if not both, of the web described herein is free of mooring yarns, framing yarns, and spiral yarns.

In some embodiments, the mooring yarns may extend radially from the framing yarns in a manner aligned with a center of the web but without traversing the framing yarns and/or any of the axial, radial, or spiral yarns. In some embodiments, the mooring yarns may extend in a non-radially manner from the framing yarns but without traversing the framing yarns and/or any of the axial, radial, or spiral yarns.

In some embodiments, the mooring yarns may be equally spaced about the framing yarns. In some embodiments, the mooring yarns may extend symmetrically around the outer peripheral edge of the web.

Framing yarns and mooring yarns are configured to provide additional strength and support to the web. In particular, the framing yarns are configured to help hold the axial, radial and/or spiral yarns together within the defined perimeter of the framing yarns, and the mooring yarns are configured for anchoring the web into tissue upon implantation.

In some embodiments, the diameter of the mooring yarns is greater than or equal to the diameter of the framing yarns. The term diameter is referred to herein without intending to limit the yarn to having only a round cross-section, non-round cross-sections are also intended.

In some embodiments, the diameter of the framing yarns is greater than or equal to the diameter of the spiral yarns.

In some embodiments, the diameter of the spiral yarns is greater than or equal to the diameter of the radial and/or axial yarns.

In some embodiments, the diameter of the radial and/or axial yarns is greater than or equal to the diameter of the threading yarns.

In some embodiments, the mooring yarns and framing yarns have a greater diameter than the diameter of the axial, radial, spiral, and/or threading yarns.

In some embodiments, the spiral yarns have a greater diameter than the axial, radial, and/or threading yarns.

In some embodiments, the radial yarns have a greater diameter than the threading yarns.

In some embodiments, the axial yarns have a greater diameter than the threading yarns.

In some embodiments, the tensile strength of the mooring yarns is greater than or equal to the tensile strength of the framing yarns.

In some embodiments, the tensile strength of the framing yarns is greater than or equal to the tensile strength of the spiral yarns.

In some embodiments, the tensile strength of the spiral yarns is greater than or equal to the tensile strength of the radial and/or axial yarns.

In some embodiments, the tensile strength of the radial and/or axial yarns is greater than or equal to the tensile strength of the threading yarns.

In some embodiments, the mooring yarns and framing yarns each have a greater tensile strength than the tensile strength of the axial, radial, spiral, and/or threading yarns.

In some embodiments, the mooring yarns, framing yarns, and radial yarns each have a greater tensile strength than the spiral yarns.

f. Vertical, Horizontal, and Diagonal Yarns

The webs described herein may further include at least one vertical, horizontal, or diagonal yarn. Vertical yarns extend longitudinally along a length of the web while horizontal yarns extend along a width of the web. The vertical and horizontal yarns extend perpendicular to each other. Diagonal yarns extend at an angle relative to the vertical or horizontal yarns and are not parallel or perpendicular to either the vertical or horizontal yarns.

Vertical, horizontal, and diagonal yarns, unlike the axial yarn, can be positioned on any portion of the web and do not need to be positioned along a central axis. Unlike radial yarns, vertical yarns remain parallel to each other across the at least one face, if not both, of the web. Unlike radial yarns, horizontal yarns remain parallel to each other across the at least one face, if not both, of the web. Unlike radial yarns, diagonal yarns remain parallel to each other across the at least one face, if not both, of the web. Unlike spiral yarns, the vertical, horizontal, and diagonal yarns do not form closed loops or spirals and can pass through the center of the web. Like all laid yarns described herein, vertical, horizontal, and diagonal yarns use threading yarns to be held into position relative to the other laid yarns of the implantable webs described herein.

In some embodiments, the implants described herein may include a plurality of vertical yarns.

In some embodiments, the implants described herein may include a plurality of horizontal yarns.

In some embodiments, the implants described herein may include a plurality of diagonal yarns.

In some embodiments, the implants described herein may include a plurality of vertical yarns and horizontal yarns.

In some embodiments, the implants described herein may include a plurality of vertical yarns and diagonal yarns.

In some embodiments, the implants described herein may include a plurality of diagonal yarns and horizontal yarns.

In some embodiments, the implants described herein may be free of vertical yarns.

In some embodiments, the implants described herein may be free of horizontal yarns.

In some embodiments, the implants described herein may be free of diagonal yarns.

In some embodiments, the implants described herein may include some combination of vertical, horizontal, and/or diagonal yarns each having the same diameter.

In some embodiments, the implants described herein may include some combination of vertical, horizontal, and/or diagonal yarns having a larger diameter than the spiral yarn and threading yarns.

In some embodiments, a vertical, horizontal, and/or diagonal yarn may extend beyond the outer edge of the web, which may be defined by the outermost spiral yarn, and curl back towards the central area, center or axial yarn of the web. In such embodiments, the vertical, horizontal, and/or diagonal yarn crosses over the outer edge of the web or the outermost spiral yarn twice to form a vertical, horizontal, and/or diagonal loop, respectively, therebetween. Like mooring yarns, the vertical, horizontal, and/or diagonal loops are suitable for anchoring the webs into tissue and may extend any distance beyond the outer edge or outermost spiral yarn.

In some embodiments, the webs described herein may include vertical yarns which all form vertical loops. In some embodiments, the webs described herein may include only vertical yarns which do not form vertical loops. In some embodiments, the webs described herein may include both vertical yarns which do not form vertical loops and vertical yarns that do form vertical loops.

In some embodiments, the webs described herein may include horizontal yarns which all form horizontal loops. In some embodiments, the webs described herein may include only horizontal yarns which do not form horizontal loops. In some embodiments, the webs described herein may include both horizontal yarns which do not form horizontal loops and horizontal yarns that do form horizontal loops.

In some embodiments, the webs described herein may include diagonal yarns which all form diagonal loops. In some embodiments, the webs described herein may include only diagonal yarns which do not form diagonal loops. In some embodiments, the webs described herein may include both diagonal yarns which do not form diagonal loops and diagonal yarns that do form diagonal loops.

g. Reinforcing Yarns

The webs described herein may further include at least one reinforcing yarn. The reinforcing yarns are added to an area of at least one face of the implant to increase the concentration of laid yarns in a certain area(s) create a reinforcement zone or member on at least one face of the implant. The reinforcing yarns, like the other laid yarns, require the addition of the threading yarns to lock the reinforcing yarns into position relative to the other laid yarns in the reinforced area of the implant. However, unlike the other laid yarns, the reinforcing yarns can be positioned in any direction or combination of directions to form any design suitable for increasing the concentration of yarns in a given area of the web to strengthen the web. For example, the reinforcing yarns may extend: in a radial manner (similar to radial yarns); in a spiral manner (similar to spiral yarns); in an axial manner (similar to axial yarns); parallel to a central axis of the implant; perpendicular to a central axis of the implant; and any combination thereof to form a reinforcement member or zone on at least one face of the implant.

The reinforcing yarns and/or the reinforcement member or zone formed therefrom may be continuous or discontinuous around at least one face of the implant. In some embodiments, the reinforcement member is in the form of a continuous loop positioned on at least one face of the web and extending around the central area of the face. In some embodiments, the reinforcing yarns used to form the reinforcement member may extend in a spiral manner in a higher concentration over the reinforced area and between a portion of the spiral yarns. Alternatively, in some embodiments, the reinforcing yarns used to form the reinforcement member or zone may extend in a radial manner in a higher concentration over the reinforced area and between a portion of the radial yarns.

In other embodiments, the reinforcement member may be discontinuous and may form a plurality of tabs positioned around the outer perimeter of the implant. In such embodiments, the reinforcing yarns used to form the plurality of reinforcement members may be intermittently dispersed around the outer perimeter of the implant and may extend in a spiral manner or a radial manner between a combination of spiral and/or radial yarns of the web. Various other shapes and/or designs are depicted in the figures and described in more detail herein.

In some embodiments, the reinforcement member or zone is positioned on one face of the implant. In some embodiments, the reinforcement member or zone is positioned on both faces of the implant.

With the use of tailored fiber placement as described hereinbelow in more detail, a higher concentration of reinforcing yarns may be laid in certain areas of the web to create fixation reinforced zones for fixation and/or reinforced zones for additional support of the closure of the soft tissue defect.

2. Threading Yarns

As previously noted, the laid yarns, i.e., axial yarns, radial yarns, spiral yarns, framing yarns, mooring yarns, vertical yarns, horizontal yarns, diagonal yarns, and/or reinforcing yarns, are held or locked into an overlapping or crisscrossing position relative to each other by threading yarns forming locking stitches around the laid yarn at or near the overlap or crisscross. The locking stitches secure the laid yarns into position relative to each other to form and/or maintain the overall structure of the implantable web.

To form the locking stitches, the implantable webs described herein include at least a first and second threading yarn that can be interlaced. Additional threading yarns may be used. The first and second threading yarns may be top and bottom threading yarns, in that the first and second threading yarns approach the laid yarns, i.e., axial, radial, spiral, framing, mooring yarns, and/or reinforcing yarns from above and below the yarns (or substrate) when laid into free-flowing position relative to each other.

Figure 2A:
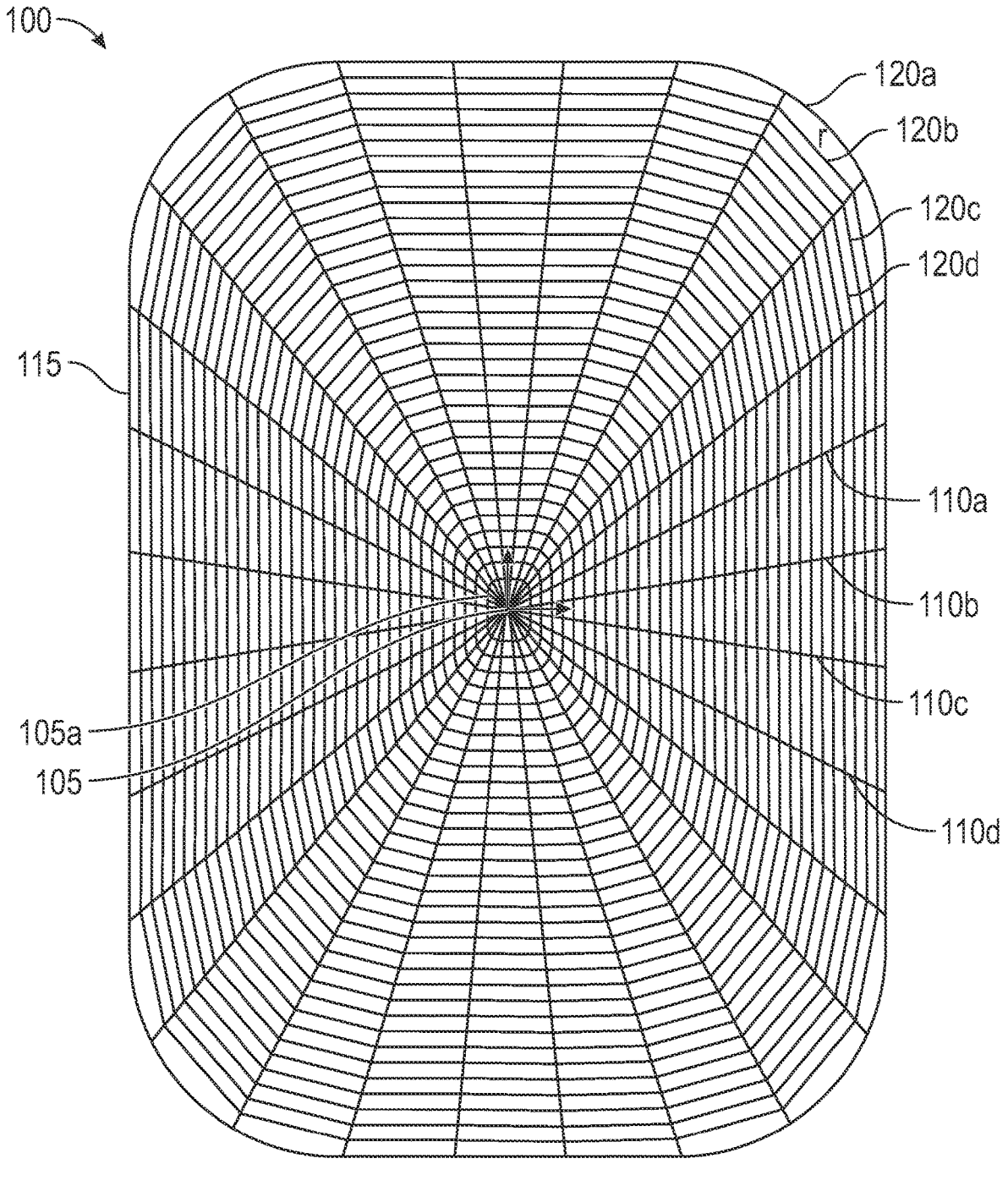
FIG. 2A is a top view of a surgical implant including a web including laid yarns and threading yarns as described in at least one embodiment herein.
Figure 2B:
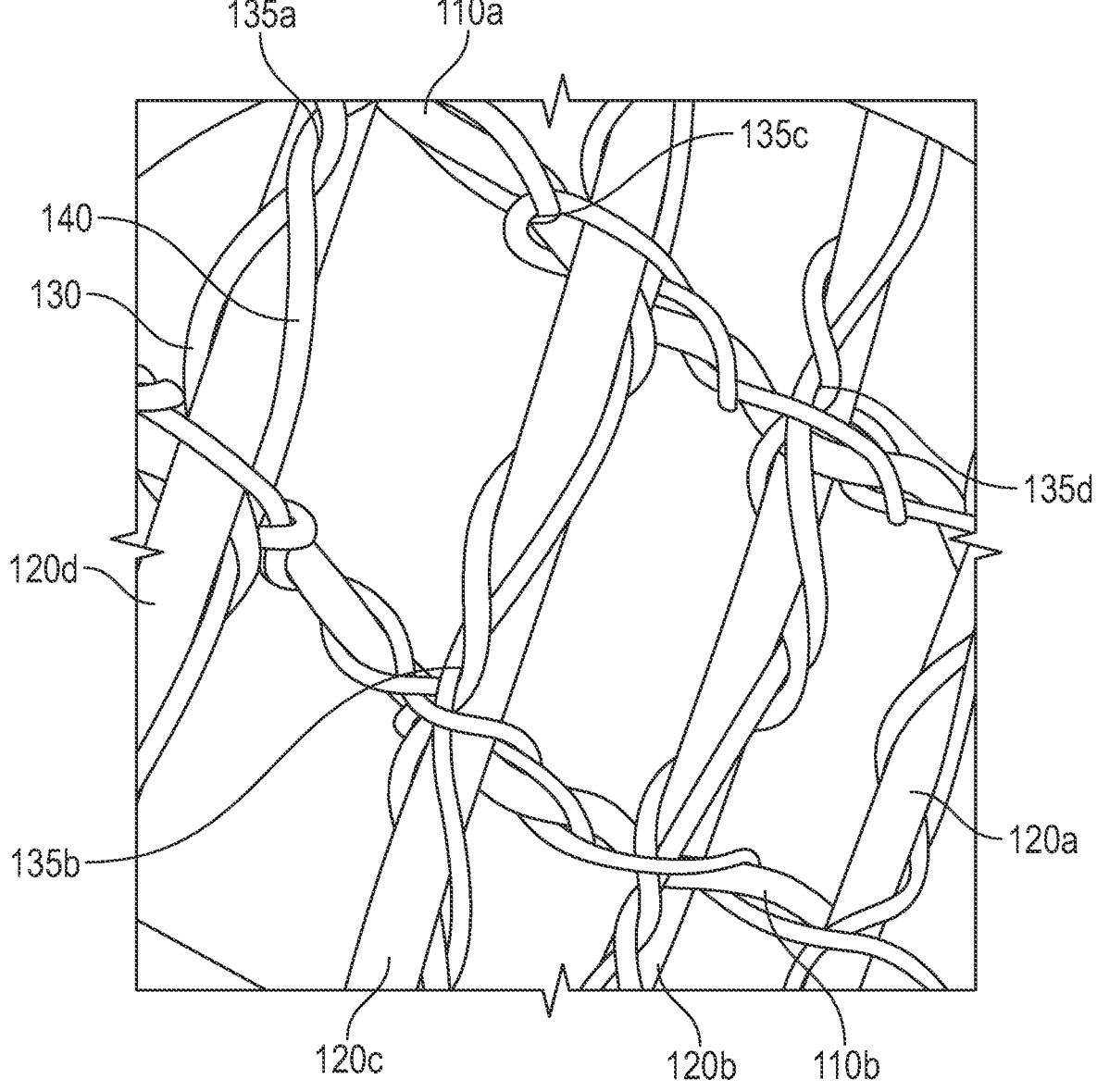
FIG. 2B is an exploded perspective view of the laid yarns and threading yarns combined to form the webs described in at least one embodiment herein.

As shown in more detail in FIG. 2B, the first and second threading yarns are interlaced together to form a locking stitch around an individual laid yarn at or near a point of intersection between different types of laid yarns. The threading yarns form a plurality of locking stitches at or near the plurality of intersections where the laid yarns crisscross or overlap. In between each of the locking stitches, the threading yarns extend generally alongside the laid yarns with or without crossing over each other.

The threading yarns also add a rigidity and/or tension to the overall structure of the web and provides the webs described herein with a memory effect, i.e., the ability of the web to return to its original planar configuration upon deployment. For example, the threading yarns may add sufficient rigidity or tension to allow the web to be folded and/or rolled for delivery to the site of implantation (via open or laparoscopic procedures) while maintaining the ability to automatically unfold or unroll to return to the original generally planar configuration after delivery and/or upon deployment.

In some embodiments, the diameter of the threading yarns may be smaller than the diameter of at least one laid yarn.

In some embodiments, the diameter of the threading yarns may be smaller than all of the laid yarns.

In some embodiments, the threading yarns may be multifilament and the laid yarns may be monofilaments.

In some embodiments, the threading yarns may be monofilaments and the laid yarns may be monofilaments.

3. Suture Assembly

In addition to the various laid yarns and threading yarns, the implants described herein may further include at least one suture assembly. A suture assembly includes a length of suture having a body positioned between a first and second end portion, wherein the first and second end portions are fixed to at least one face of the implant and/or web with the body portion free of the implant and/or web to form a loop or handle. The suture can be monofilament suture, multifilament suture, or any combination thereof.

The implant and/or web may include any number of suture assemblies. In some embodiments, the webs described herein include a single suture assembly centered on a face of the web. In some embodiments, the webs described herein include two suture assemblies, wherein each suture assembly is centered on a face of the web. In some embodiments, the webs described herein include a plurality of suture assemblies, wherein the plurality of suture assemblies are symmetrically distributed across at least one face of the web.

The at least one suture assembly may be fixed to the webs using any suitable method. In some embodiments, the suture assembly may be attached to the web using the threading yarns. In some embodiments, the suture assembly may be attached to the web using a conventional method, such as knitting, weaving, braiding, etc., the end portions of the suture assembly to the yarns of the web and/or the substrate. In some embodiments, the suture assembly may be attached using an adhesive material to adhere the end portions of the suture assembly to the yarns of the web and/or the substrate.

At least one suture assembly may further include a tubular cover surrounding a majority of the length of the suture assembly extending from the surface of the implant. The tubular cover, like the suture assembly, can be made of any biocompatible material, including any bioabsorbable or non-bioabsorbable materials, alone or in any combination.

II Substrate (or Base Material)

The implants described herein may further include a substrate on which the laid yarns and threading yarns of the implantable web may be combined. The substrate may be a permanent part of the implant or alternatively may be removed from the implant sometime prior to implantation.

The substrate may be made from any biocompatible material suitable for implantation including any bioabsorbable material and/or any non-bioabsorbable material, alone or in combination.

In some embodiments, the substrate is a textile made from conventional methods, such as knitting, braiding, weaving, etc. and includes interwoven yarns, such as warp and weft threading. Some examples of suitable textiles are described in U.S. Pat. Nos. 7,331,199 and 9,186,235, which are incorporated by reference herein. In some embodiments, the substrate may be a knit textile. In some embodiments, may be a Pro-Grip® mesh.

In some embodiments, the substrate is a dissolvable backing material, such as a cloth or textile. The dissolvable substrate may be formed from acetate or any other material suitable for use as a dissolvable substrate. Dissolvable substrate materials are chosen such that the dissolution process or processes used to remove the dissolvable substrate will have minimal effects on the physical properties of the yarns of the web which are designed to remain after dissolution.

In some embodiments, the substrate is made of a material which dissolves when placed in contact with water, saline or other natural bodily fluids including blood, mucous, sweat, saliva and the like. Some examples of such dissolvable materials include, but are not limited to, polyvinyl pyrrolidones, polyethylene glycols, polyvinyl alcohols, polyacrylic acids, carboxymethylcellulose, alginates, hyaluronic acids, dextrans, polysaccharides, gelatins, and combinations thereof.

In some embodiments, the implants include an implantable web and a substrate. In some embodiments, the substrate may be larger in surface area than the web thereby expanding beyond the outer peripheral edge of the web to define the outer peripheral edge of the implant.

III. Methods of Forming the Implants

The implants described herein, and particularly the implantable webs described herein may be formed using tailored fiber placement technology (TFP). TFP is a process based on the principle of placing and sewing continuously at least one yarn onto a substrate in almost any desired direction to create a textile. In the present case, TFP technology is used to place and secure the axial yarns, radial yarns, spiral yarns, framing yarns, mooring yarns, vertical yarns, horizontal yarns, diagonal yarns, and/or reinforcing yarns as described herein onto a substrate, via the interlacing of at least a first and second threading yarns.

Figure 1B:
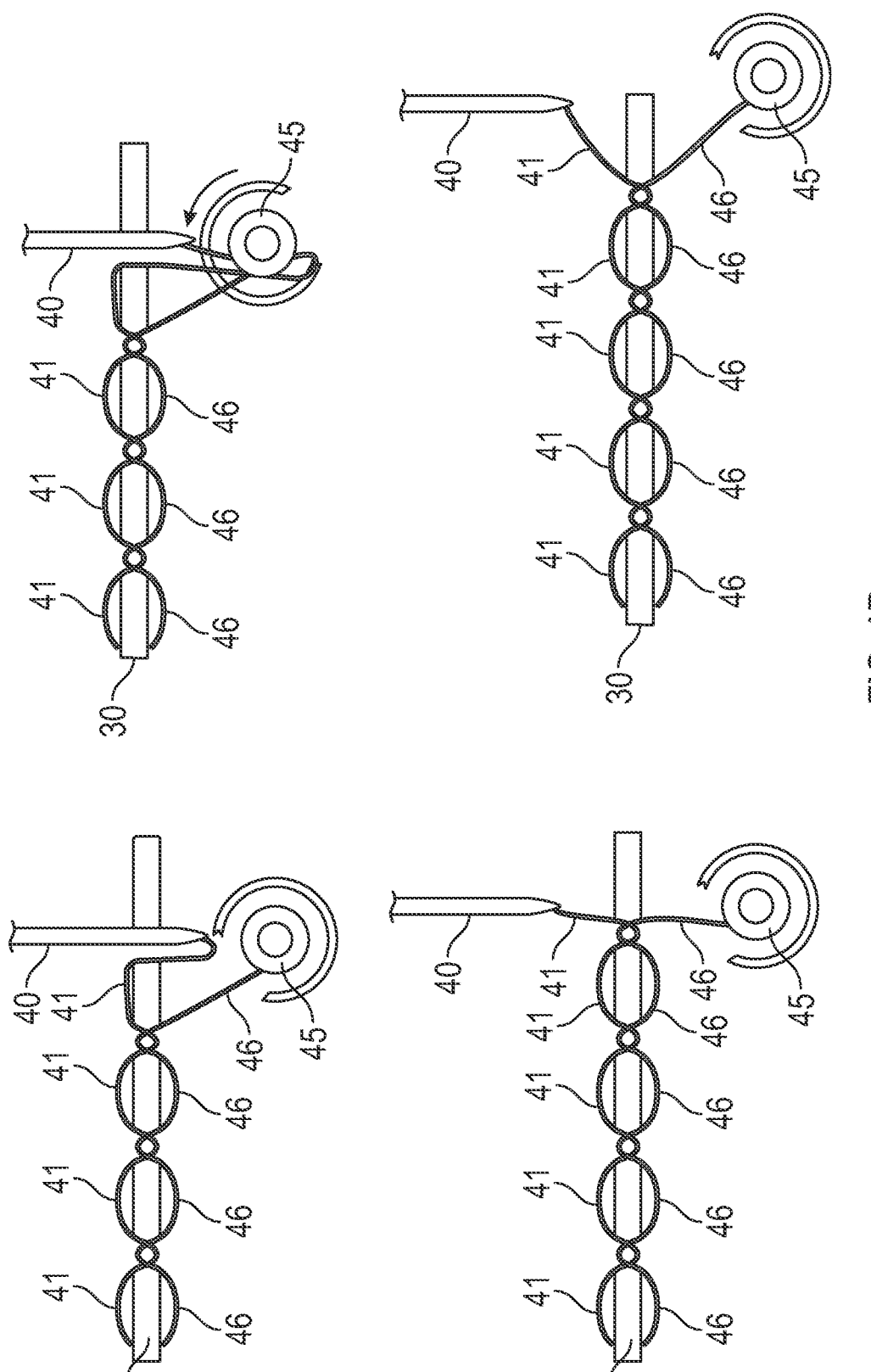

As illustrated in FIGS. 1A-1B, TFP technology uses a system which includes at least one laid bobbin storing laid yarn 20 (representing at least one of the axial yarns, radial yarns, spiral yarns, framing, yarns, mooring yarns, vertical yarns, horizontal yarns, diagonal yarns, and/or reinforcing yarns) and laid guide element 10 for determining where to lay or place laid yarn 20 onto substrate or base material 30 in a specifically tailored manner. Laid yarn 20 is placed on the substrate 30 ahead of thread needle 40 and thread bobbin 45. Thread needle 40 is positioned on the same side of the substrate 30 as laid yarn 20 and thread bobbin 45 is positioned on an opposite side of substrate 30. First threading yarn 41 and second threading yarn 46 are connected to thread needle 40 and thread bobbin 45, respectively. After laid guide element 10 lays laid yarn 20 on substrate 30, thread needle 40 including first threading yarn 41 pierces substrate 30 passing first threading yarn 41 through substrate 30 and into thread bobbin 45. Thread bobbin 45 includes a shuttle hook 47 which moves to catch first threading yarn 41 and carry first threading yarn 41 around second threading yarn 46. Thread needle 40 then rises to return to its original position on the top side of substrate 30 pulling both the first and second threading yarns 41, 46 to form locking stitches around laid yarn 20 and substrate 30, thereby locking laid yarn 20 into a position on substrate 30 and/or locking laid yarn 20 into a position relative to other laid yarns. As needle thread 40 rises, some combination of laid guide element 10, thread needle 40, thread bobbin 45, and substrate 30 are advanced to a new position. Laid guide element 10 is designed to rotate on itself 360 degrees (as indicated by arrows), which allows laid yarn 20 to be placed onto substrate 30 following a tailor made design.

Substrate 30 may be positioned on a movable tray or frame (not shown), which can move the substrate in any three-dimensional direction.

The system, including the needles, bobbins and/or the tray (or frame), may be controlled by a computer and/or computer software.

The threading yarns play a key role in linking all laid yarns to the substrate and also to keep the various types of laid yarns linked together as a single web structure, before, during, and/or after at least a portion of the substrate, if not the entire substrate, is removed.

TFP, unlike conventional techniques such as knitting, braiding, and/or weaving, is more flexible from a design standpoint, in that the fiber orientation, fiber concentration, and web geometry can be easily tuned as needed to better adapt the mechanical behavior of the webs to the patient's physiology and/or to address the various possible stresses commonly associated with certain types of activities performed post-procedurally, such as jogging, walking, coughing, breathing, bending, etc.

Moreover, because TFP ensures a high level of accuracy and repeatability in the quantity and orientation of the fiber lay down process, as compared to conventional techniques, the mechanical behaviors of a specific web configuration formed by TFP is easier to predict through simulation during development and/or in advance of implantation.

In addition, because TFP can provide an implantable web of a tailored design, TFP utilizes less material than conventional techniques and thus there is less material loss and therefore less cost associated with the individual webs produced by TFP.

In some embodiments, methods are of forming an implantable web for soft tissue repair as described herein may include the steps of: a) providing a substrate onto a movable tray, b) laying a plurality of laid yarns onto a first side of a substrate via a laying guide element, c) threading a needle including a first threading yarn from the first side of the substrate through the substrate to a second side of the substrate and around a second threading yarn, d) returning the needle to the first side of the substrate with a portion of the first and second threading yarns to form a locking stitch around at least one of the plurality of laid yarns and locking the laid yarn into position on the substrate and relative to other laid yarns, and e) advancing some combination of the movable tray, substrate, laying guide element, or needle to extend the first and second threading yarns along the laid yarn a certain length before repeating steps c) and d).

IV. Implants

Turning now to the figures, exemplary implants as described herein are shown and will be discussed in additional detail, without any intent to limit the scope of the implants specifically only to those depicted.

As shown in FIG. 2A, a surgical web 100 includes a plurality of radial yarns 110a-d extending in a radial direction from a central area 105, in particular the center 105a, of the web 100 to an outer peripheral edge 115 of the web 100 and a plurality of spiral yarns 120a-d turning around the central area 105 of the web 100 and extending between the plurality of radial yarns 110a-d. Each spiral yarn 120a-d connects neighboring radial yarns 110a-d. Alternatively, each radial yarn 110a-d connects neighboring spiral yarns 120a-d.

Spiral yarns 120a-d are neighboring spiral yarns spaced apart by a radial distance r. As shown, the radial distance r is constant and/or the same for spiral yarns 120a-d. In some embodiments, spiral yarns 120a-d do not traverse the central area 105 and particularly, the center 105a positioned within the central area 105 of the web 100.

As further shown in FIG. 2A, in some embodiments, the outermost spiral yarn 120a may represent the outer peripheral edge 115 of the web 100. In addition, the plurality of the spiral yarns 120a-d may extend generally parallel to each other around the central area 105 of the web 100 and/or may be evenly spaced around the central area 105 of the web 100.

As shown in the expanded portion of FIG. 2B, the radial yarns 110a-b overlap or crisscross spiral yarns 120a-d but are not interwoven with the spiral yarns 120a-d, and at least a first threading yarn 130 and a second threading yarn 140 extend generally along the length of at least one of the radial yarns 110a-b and/or spiral yarns 120a-d. As further shown in FIG. 2B, the first and second threading yarns 130, 140 interlace each other intermittently along the length of the radial yarns 110a-b and/or spiral yarns 120a-d to form a plurality locking stitches 135a-c. The locking stitches 135a-d hold the radial yarns 110a-b and spiral yarns 120a-d in a position relative to each other to form and/or maintain the overall structure of the web 100.

Although the locking stitches 135a-d are depicted in FIG. 2B on each of the laid yarns, i.e., the radial yarns 110a-b and the spiral yarns 120a-d, it is envisioned that in some embodiments the locking stitches may be on only one of the laid yarns, i.e., radial or spiral yarns. It is further envisioned that the webs described herein may include any number of locking stitches sufficient to form and/or maintain the overall structure of the web.

In some embodiments, as illustrated in FIG. 2B, at least one, and in particular two, locking stitch(es) are formed on the length of each of the radial yarns 110a-b positioned between each intersection, i.e., where radial yarns 110a-b crisscross or overlap spiral yarns 120a-d.

In some embodiments, as further illustrated in FIG. 2B, at least one, and in particular two, locking stitch(es) are formed on the length of each of the spiral yarns 120a-d positioned between each intersection, i.e., where radial yarns 110a-b crisscross or overlap spiral yarns 120a-d.

FIG. 2B also depicts that in some embodiments the threading yarns 130, 140 may be smaller in diameter (or cross-sectional size for non-circular shapes) than the laid yarns, i.e., radial yarns 110a-b and/or spiral yarns 120a-d.

In some embodiments, the ratio of the diameters (or cross-sectional size for non-circular shapes) of the threading yarns to the radial yarns and the spiral yarns may range from about 1:1:1 to about 1:3:3, respectively.

FIG. 2B further depicts that in still other embodiments, the threading yarns 130, 140 may be smaller in diameter (or cross-sectional size for non-circular shapes) than the radial yarns 110a-b, which may be smaller in diameter (or cross-sectional size for non-circular shapes) than the spiral yarns 120a-d.

In such embodiments, the ratio of the diameters (or cross-sectional size for non-circular shapes) of the threading yarns to the radial yarns and the spiral yarns is about 1:2:3, respectively.

Figure 3:
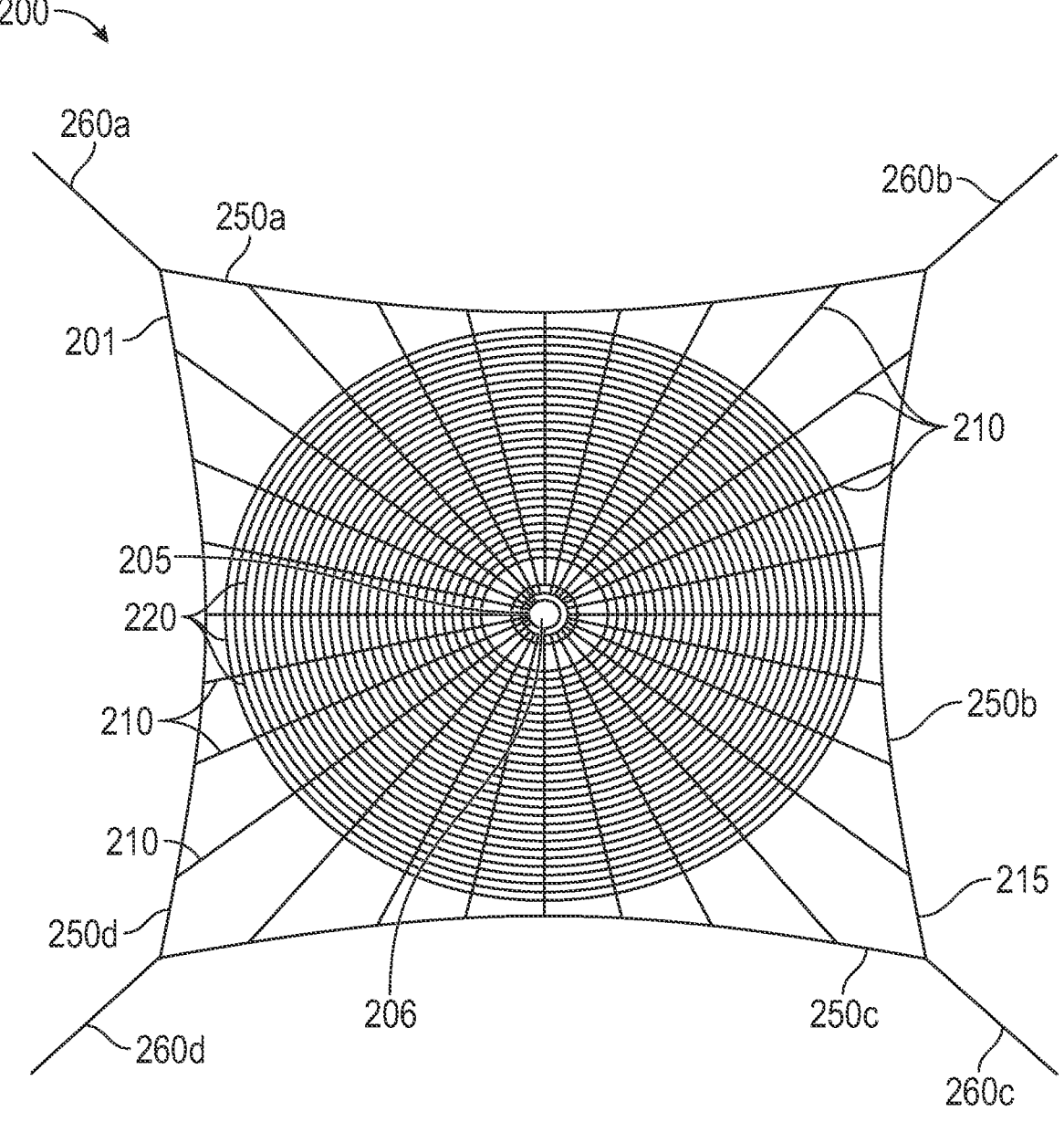
FIG. 3 is a top view of a surgical implant including a web including laid yarns and threading yarns as described in at least one embodiment herein.

Turning now to FIG. 3, implant 200 includes implantable web 201 formed from a plurality of radial yarns 210 extending in a radial direction from a central area 205 surrounding a central aperture 206 to an outer peripheral edge 215 of the web 201 defined by framing yarns 250a-d. Web 201 further includes a plurality of spiral yarns 220 turning around the central area 205 of the web 201 and extending between the plurality of radial yarns 210. Spiral yarns 220 connect neighboring radial yarns 210. As shown, the spiral yarns 220 do not traverse the central aperture 206 of the web 201. At least first and second threading yarns are also present but not shown in expanded view.

Central aperture 206 is free of any yarns, including specifically threading yarns, axial yarns, radial yarns, spiral yarns, framing yarns, and/or mooring yarns.

Surgical web 201 further includes framing yarns 250a-d and mooring yarns 260a-d wherein the framing yarns 250a-d define the outer peripheral edge 215 of the web 201 and the mooring yarn 260a-d extend away from the framing yarns 250a-d and/or the outer peripheral edge 215 of web 201.

As depicted in FIG. 3, the radial yarns 210 extend beyond the outermost spiral yarn 220 (spiral yarn furthest from central area 205) to framing yarns 250a-d thereby creating a zone Z near the peripheral outer edge 215 free of spiral yarns 220 and/or including only radial yarns 210 (and optionally threading yarns). The length of the radial yarns may vary in the zone Z.

Framing yarns 250a-d are displaced a radial framing distance f from the outermost spiral yarn 220. As illustrated, the radial framing distance f may vary around the web 201 and/or the radial framing distance f is greater than the radial distance r between at least some, if not all, of the spiral yarns 220.

In some embodiments, the webs described herein may include a constant radial distance r and a varying radial framing distance f.

As further depicted in FIG. 3, mooring yarns 260a-d extend radially from framing yarns 250a-d in a manner aligned with the center aperture 206 of the web 201 located in central area 205. It is envisioned that mooring yarns may also extend in a non-radially manner alone or in combination with the mooring yarns that extend radially.

As shown in FIG. 2B in the expanded view, and similarly applicable to the web 201 and the laid yarns, i.e., radial yarns, spiral yarns, framing yarns, and/or mooring yarns, of FIG. 3 (not shown in expanded view), at least a first threading yarn and a second threading yarn are interlaced to each other to form locking stitches about the laid yarns, i.e., the radial yarns, the spiral yarns, the framing yarns, and/or the mooring yarns (not all shown), to hold each of the laid yarns in a position relative to each other to form and/or maintain the overall structure of the web 201. In some embodiments, the locking stitches may be positioned on or around at least two of the laid yarns to hold the plurality of laid yarns in a position relative to each other to maintain the structure of the web.

Turning now to FIGS. 4A-4D, implant 300 is depicted including web 301 formed from at least one axial yarn 307, a plurality of radial yarns 310, and a plurality of spiral yarns 320. As depicted specifically in FIG. 4A, one axial yarn 307 extends along a central longitudinal axis CLA of the web 301 between a proximal end 307a and a distal end 307b of the axial yarn 307. Axial yarn 307 does not extend to the outer peripheral edge 315 of the web 301. It is envisioned that in some embodiments, the at least one axial yarn may extend along the central traverse axis CTA rather than the CLA.

Figure 4A:
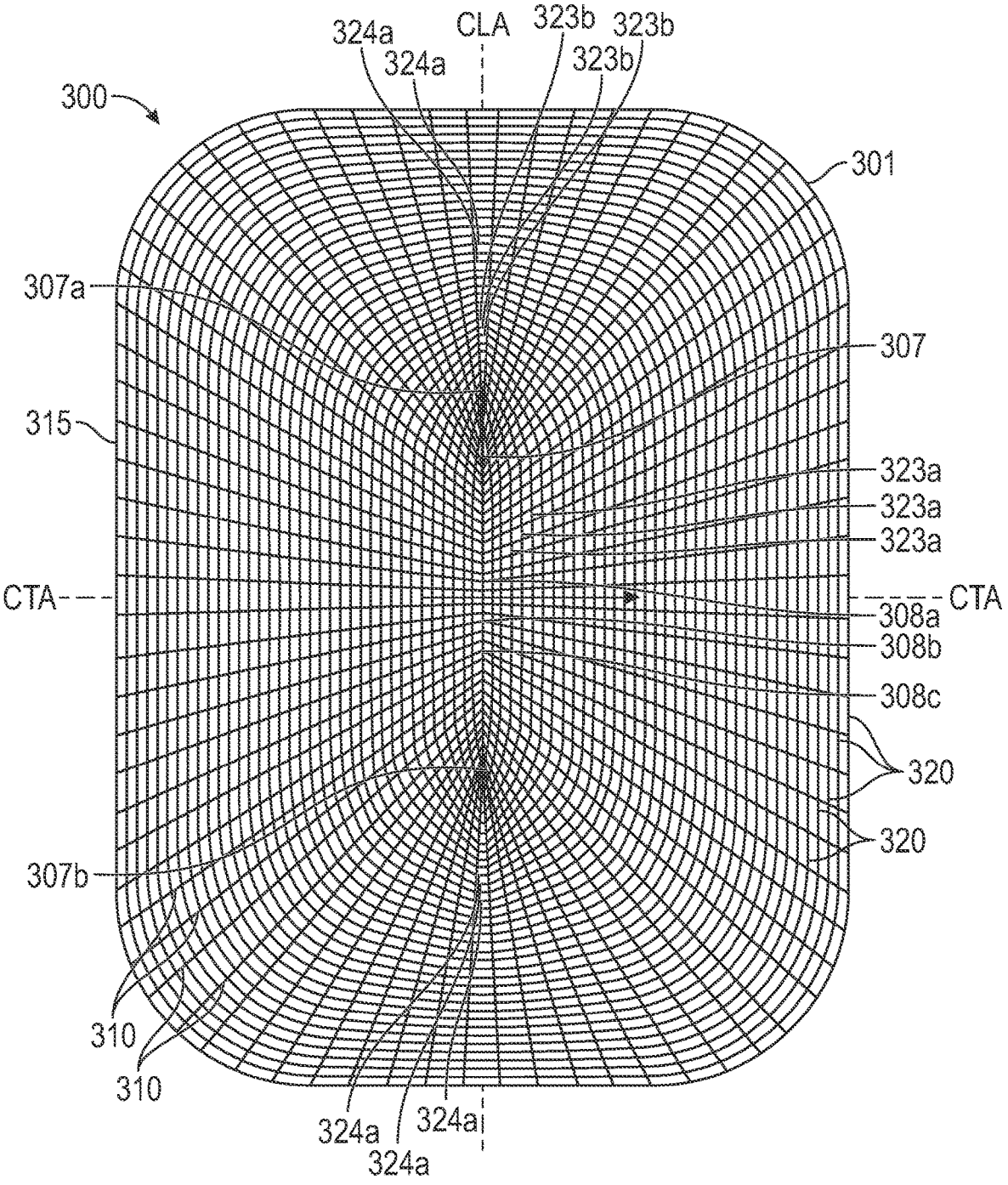
FIGS. 4A-4D are top views of a surgical implant including a web including laid yarns and threading yarns as described in at least one embodiment herein.

As further depicted in FIG. 4A, the plurality of radial yarns 310 extend in a radial direction from at least one location 308a, and sometimes multiple different locations 308a-c, along the length of axial yarn 307. The plurality of spiral yarns 320 being spaced from and turning around axial yarn 307 and extending between the plurality of radial yarns 310. Spiral yarns 320 connecting neighboring radial yarns 310 without traversing axial yarn 307.

As still further shown in FIG. 4A, the spiral yarns 320 can form the general shape of an ellipse, with two opposite long sides 323a, which are substantially parallel to CLA (or substantially perpendicular to the CTA), and two opposite short sides 323b, which are substantially perpendicular to the CLA (or substantially parallel to the CTA), wherein in each of the short sides 323b of the spiral yarn 320 form a first and second U-shaped bend 324a, 324b extending along the center longitudinal axis CLA towards the outer peripheral edge 315 of the web 301, with the opening in the U-shaped bend closest to the center of the web 301. In some embodiments, the general contour of the innermost spiral yarns 320 may differ from the general contour of the outer peripheral edge 315 of the web 301, as illustrated in FIG. 4A.

As shown in FIG. 2B in the expanded view, and similarly applicable to the web 301 and the laid yarns, i.e., radial yarns, spiral yarns, and/or axial yarns, of FIG. 4A (not shown in expanded view), at least a first threading yarn and a second threading yarn are interlaced to each other to form locking stitches about any combination of the laid yarns, i.e., the radial yarns, the spiral yarns, and/or the axial yarns (not all shown), to hold each of the laid yarns in a position relative to each other to form and/or maintain the overall structure of the web 301.

Figure 4B:
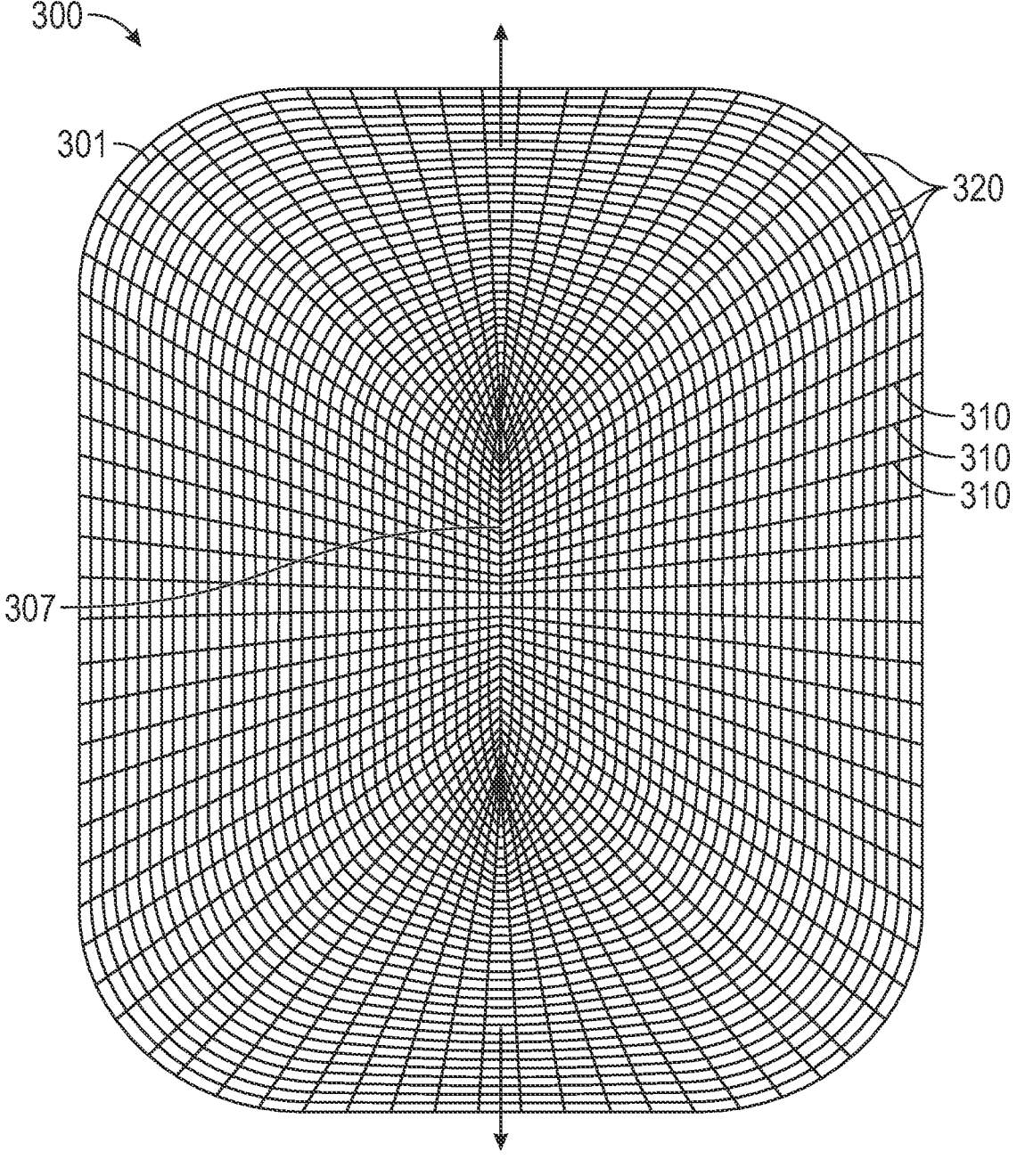
Figure 4C:
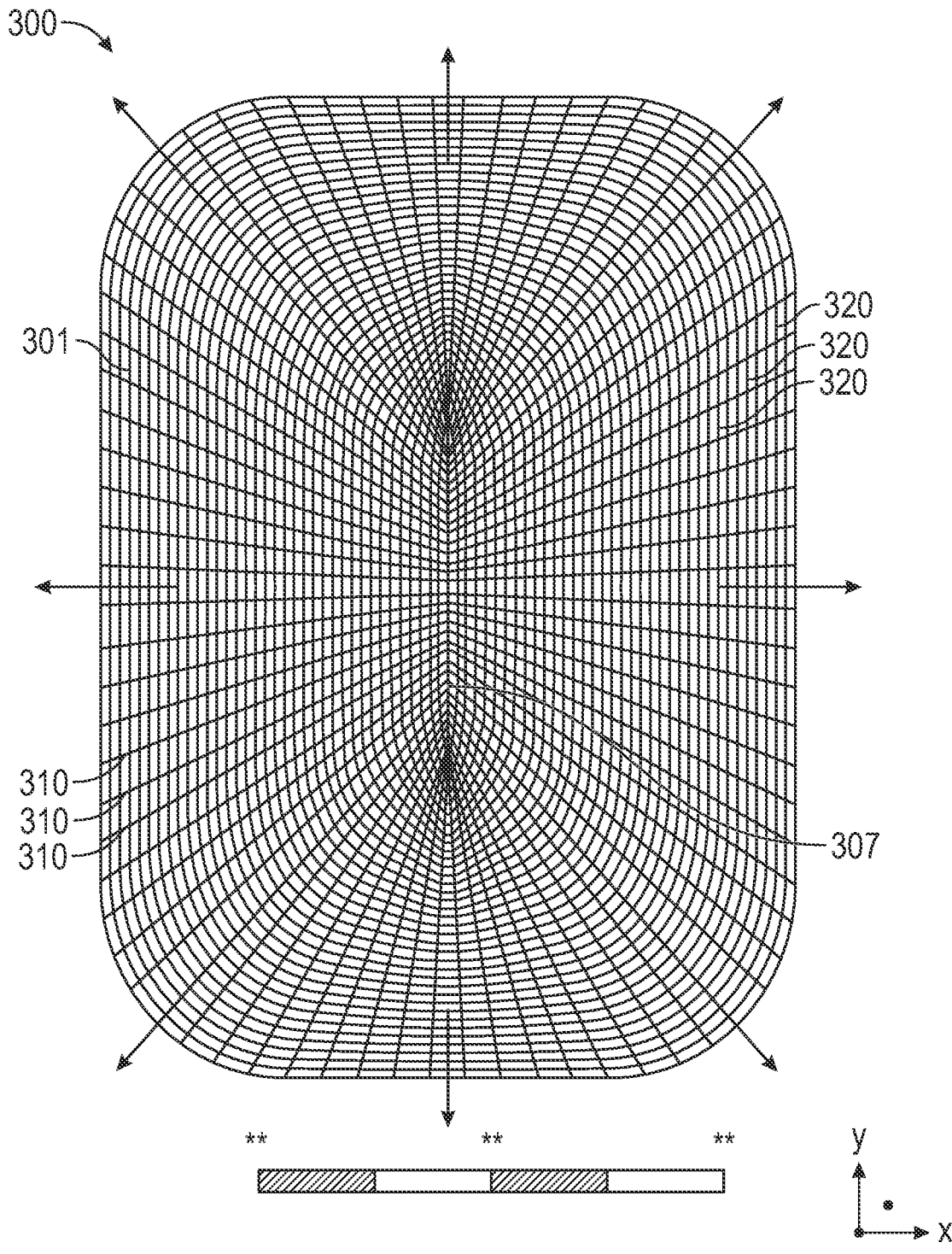
Figure 4D:
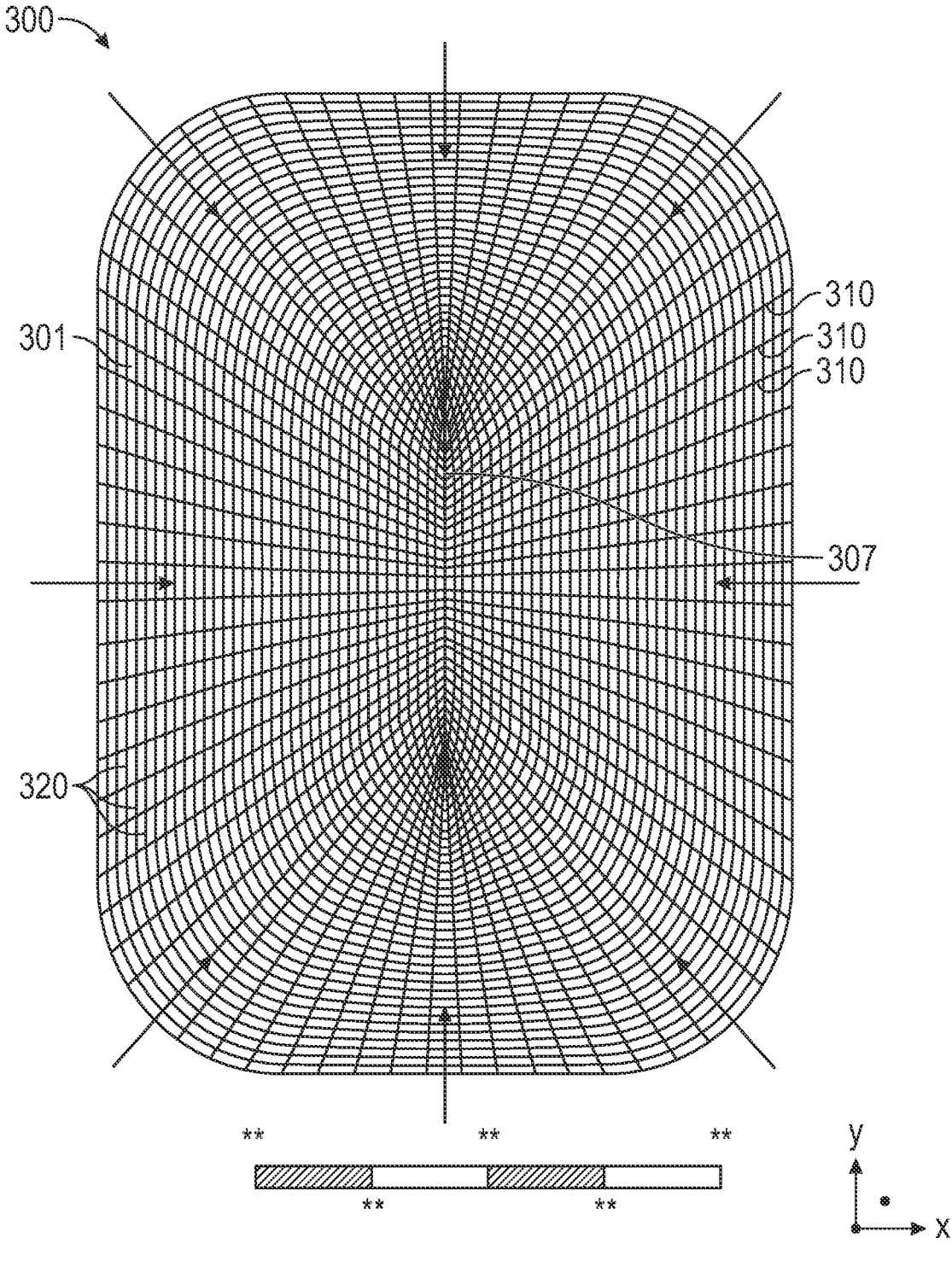

Turning now to FIGS. 4B-4D, in some embodiments, the webs 301 may include at least one radial 310 and/or axial yarn 307 having a higher degree of elasticity as compared to the spiral yarns 320. Spiral yarns 320, having a lower degree of elasticity compared to the axial and radial yarns 307, 310, will limit the stretch of the web 300 when submitted to a unidirectional or multidirectional load.

In some embodiments, exposure to a unidirectional load, such as when the web is exposed to the stress associated with normal day-to-day activities of a patient post-surgery (e.g., breathing, sitting, laying down, etc.), may cause the radial and/or axial yarns 310, 307 to stretch uniaxially in any direction, as indicated by the pair of arrows in FIG. 4B, while the less elastic spiral yarns 320 limit the rest of web 301 from being stretched. This combination of yarns improves the webs ability to adapt to unidirectional stresses in a manner which is less irritating to the wound and/or less painful to the patient on a day-to-day basis, as compared to conventional meshes produced via other textile technologies, such as knitting, braiding, weaving, etc.

In some embodiments, exposure to a multidirectional load, such as when the web is exposed to the multiple or higher level stress(es) associated with more advanced activities of a patient post-surgery (e.g., running, exercising, jumping, dancing, coughing, etc.), may cause the radial and/or axial yarns 310, 307 to stretch multiaxially, as indicated by the arrows in FIG. 4C, while the less elastic spiral yarns 320 limit the web 301 from being stretched beyond a certain level of strain defined by the less elastic (having a lower degree of elasticity than the radial and/or axial yarns) spiral yarns 320.

As indicated by the arrows depicted in FIG. 4D, the higher degree of elasticity of the radial and axial yarns 310, 307 allow the overall structure of the web 301 to return to its initial shape or configuration upon removal of the multidirectional load without any deformation and/or bulging effect commonly associated with stiff conventional surgical mesh.

This combination of yarns improves the webs ability to adapt to multidirectional stresses in a manner which maintains reinforcement functionality of the webs both during the application of the stress and after the removal of the stress, as compared to conventional meshes produced via other textile technologies, such as knitting, braiding, weaving, etc.

Due to these improved adaptive behaviors of the implants and webs described herein, individually or in combination, the patient may: experience less pain resulting from the implantable web irritating the wound tissue before and/or after exposure to every day abdominal stresses; get back to his/her daily activities faster; and/or, be less likely to experience failure of the implant to properly support the wound, as compared to patients exposed to conventional meshes produced via other textile technologies, such knitting, braiding, weaving, etc.

Figure 5:
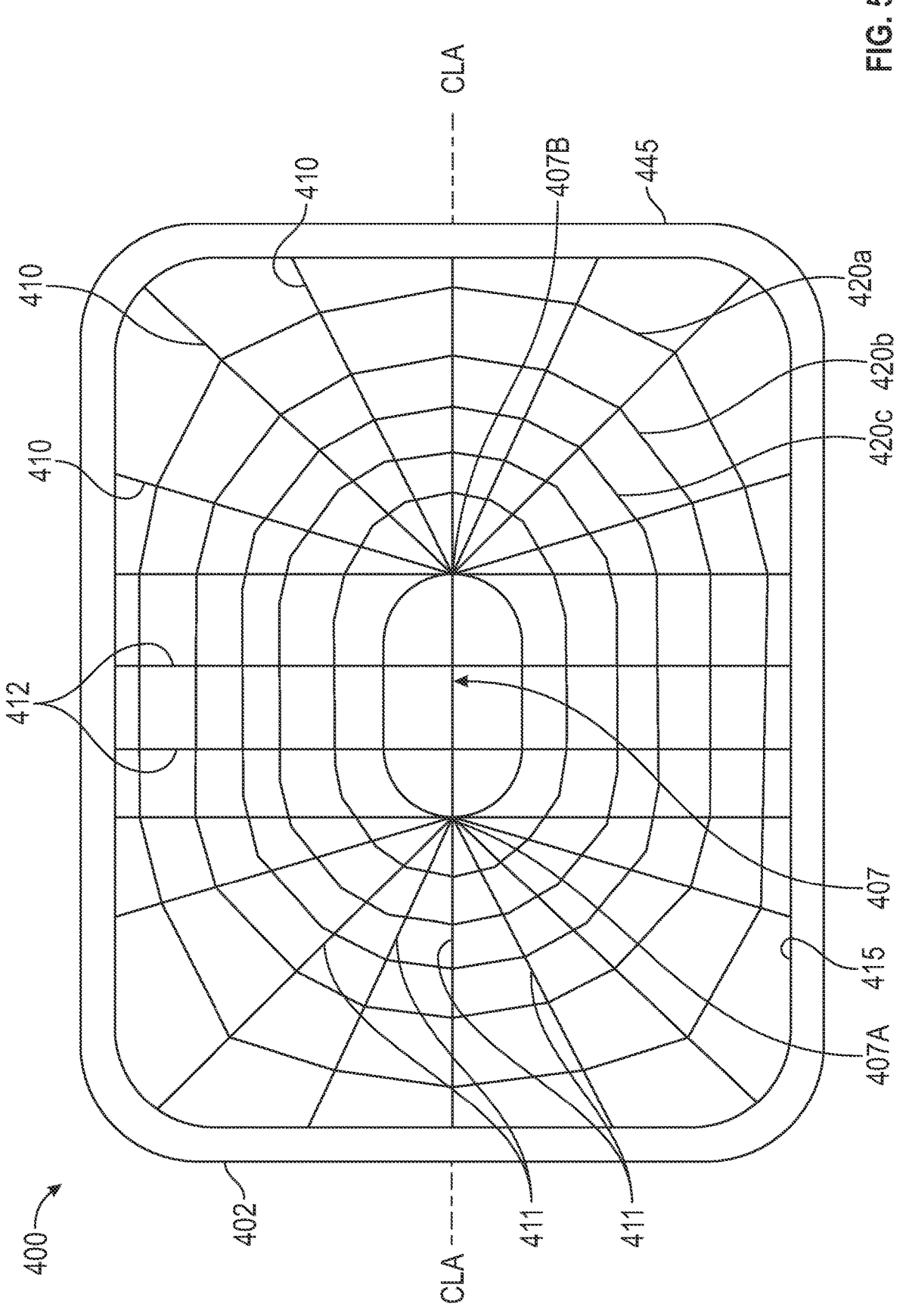
FIG. 5 is a top view of a surgical implant including a web including laid yarns and threading yarns and a substrate as described in at least one embodiment herein.

FIG. 5 illustrates an implant 400 including a web 401 made from at least one axial yarn 407, a plurality of radial yarns 410, 411, a plurality of horizontal yarns 412, and a plurality of spiral yarns 420a-c placed on and secured to a substrate 402 by threading yarns (not shown in FIG. 5, see FIG. 2A). The at least one axial yarn 407 extends along a CLA of the web 401 to the outer peripheral edge 415 of the web 401. Web 401 is shown laid on top of substrate 402 wherein substrate 402 fills in at least some, if not all, of the gaps shown between the axial, radial, spiral and horizontal yarns of web 401 and extends beyond the outer peripheral edge 415 of the web 401. In such embodiments, the outer peripheral edge 445 of substrate defines the outer peripheral edge 405 of implant 400.

As further depicted in FIG. 5, a first portion of the plurality of radial yarns 411 extend in a radial direction from a proximal end portion 407a of axial yarn 407, a second portion of the plurality of radial yarns 410 extend in a radial direction from a distal end portion 407b of axial yarn 407. The plurality of horizontal yarns 412 extend from or across a portion of axial yarn 407 positioned between the proximal and distal end portions 407a, 407b. The horizontal yarns 412 extend substantially perpendicular to the axial yarn 407, as well as the CLA, and remain parallel to each other across the face of the web 401 to the outer peripheral edge 415.

As shown in FIG. 2B in the expanded view, and similarly applicable to the web 401 and the laid yarns, i.e., axial yarns, radial yarns, spiral yarns, and/or horizontal yarns, of FIG. 5 (not shown in expanded view), at least a first threading yarn and a second threading yarn are interlaced to each other to form locking stitches about any combination of the laid yarns, i.e., the axial yarns, the radial yarns, the spiral yarns, and/or the horizontal yarns (not all shown), to hold each of the laid yarns in a position relative to each other to form and/or maintain the overall structure of the web 401.

Figure 6:
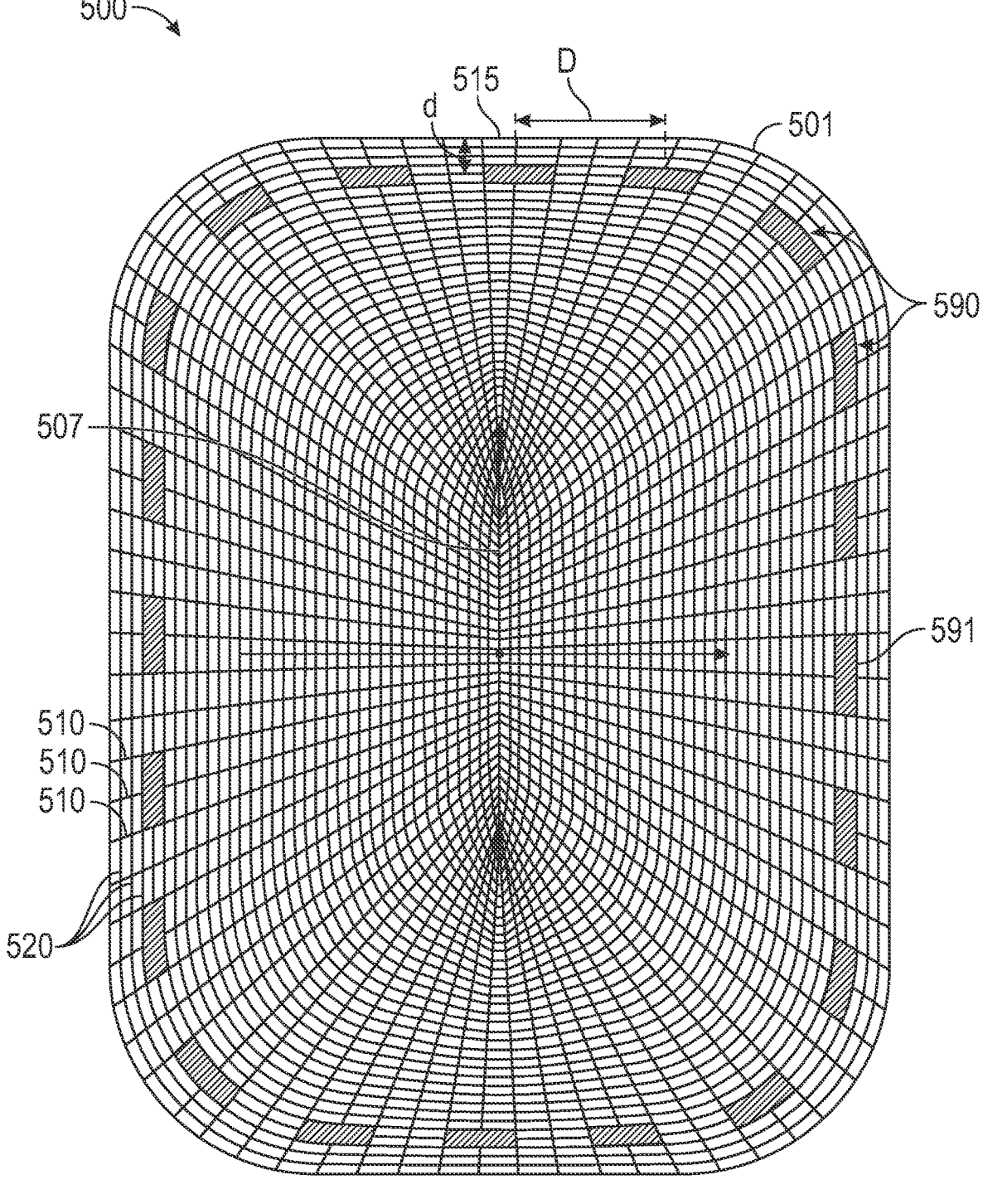
FIGS. 6-9 are top views of surgical implants including a web including laid yarns and threading yarns and at least one reinforcing zone as described in various embodiments herein.

Turning to FIG. 6, implant 500 is shown including web 501 including at least one axial yarn 507, radial yarn 510, and spiral yarn 520, and as well as at least one, and in particular a plurality of, reinforcement zone 590. Additional first and second threading yarns are also present but not shown in expanded view. In addition, in some embodiments, implant 500 and/or web 501 may further include a substrate, horizontal yarns, vertical yarns, diagonal yarns, framing yarns, and/or mooring yarns.

Reinforcement zones 590 are shown extending across the spaces between the radial yarns 510 and/or spiral yarns 520 of the web 501. The reinforcement zones 590 are formed by the addition of the reinforcing yarns 591 to the web 501. Additional threading yarns may be used to hold the reinforcing yarns 591 in place relative the radial yarns 510 and/or spiral yarns 520. Reinforcing yarns 591 extend between radial yarns 510 and/or spiral yarns 520 to at least partially fill-in the space therebetween. However, as further shown in FIG. 6, In some embodiments, the reinforcing yarns 591 of each the reinforcement zone 590 are discontinuous and may extend over a limited number of the radial yarns 510 and/or spiral yarns 520 to create multiple discontinuous reinforcement zones 590.

In some embodiments, as further depicted in FIG. 6, at least some of the reinforcement zones 590 may extend between the same number of radial yarns 510 as spiral yarns 520, i.e., extending between 2 radial yarns and 2 spiral yarns as shown. In some embodiments, all of the reinforcement zones may extend between the same number of radial yarns 510 and/or spiral yarns 520 across the entire face of the web as shown.

In some embodiments, at least some of the reinforcement zones may extend between different numbers of radial yarns as spiral yarns, i.e., extending between 2 radial yarns and 3 spiral yarns (not shown). In some embodiments, all of the reinforcement zones extend between different numbers of radial yarns and/or spiral yarns across the entire face of the web (not shown).

In some embodiments, the reinforcement zones 590 may be separated by the same number of radial yarns 510 and/or spiral yarns 520, i.e., separated by 2 radial yarns and 2 spiral yarns as shown. In some embodiments, all of the reinforcement zones 590 are separated by the same number of radial yarns 510 and/or spiral yarns 520 across the entire face of the web as shown.

In some embodiments, the reinforcement zones may be separated by a different number of radial yarns and/or spiral yarns, i.e., separated by 2 radial yarns and 3 spiral yarns (not shown). In some embodiments, all of the reinforcement zones are separated by a different number of radial yarns and/or spiral yarns across the entire face of the web (not shown).

In some embodiments, the reinforcement zone 590 may be positioned a distance d from the outer peripheral edge 515. The distance d ranging from about 0.05 cm to about 5 cm from the edge 515 of the web 501. In some embodiments, the distance d ranging from about 0.1 cm to about 2.5 cm. In some embodiments, the distance d ranging from about 0.25 cm to about 2 cm. In some embodiments, the distance d is about 0.5 cm to about 1 cm from the edge 515.

In some embodiments, the plurality of discontinuous reinforcement zones 590 may be separated from each other on the surface of the web 501 a distance D. The distance D ranging from about 0.05 cm to about 5 cm between each neighboring zone 590. In some embodiments, the distance D ranging from about 0.1 cm to about 2.5 cm. In some embodiments, the distance D ranging from about 0.25 cm to about 2 cm. In some embodiments, the distance D is about 2 cm.

As shown in FIG. 2B in the expanded view, and similarly applicable to the web 501 and the laid yarns, i.e., axial yarns, radial yarns, spiral yarns, and/or reinforcing yarns, of FIG. 6 (not shown in expanded view), at least a first threading yarn and a second threading yarn are interlaced to each other to form locking stitches about any combination of the laid yarns, i.e., the axial yarns, the radial yarns, the spiral yarns, and/or the reinforcing yarns (not all shown), to hold each of the laid yarns in a position relative to each other to form and/or maintain the overall structure of the reinforcement zones 590 and/or web 501.

Figure 7:
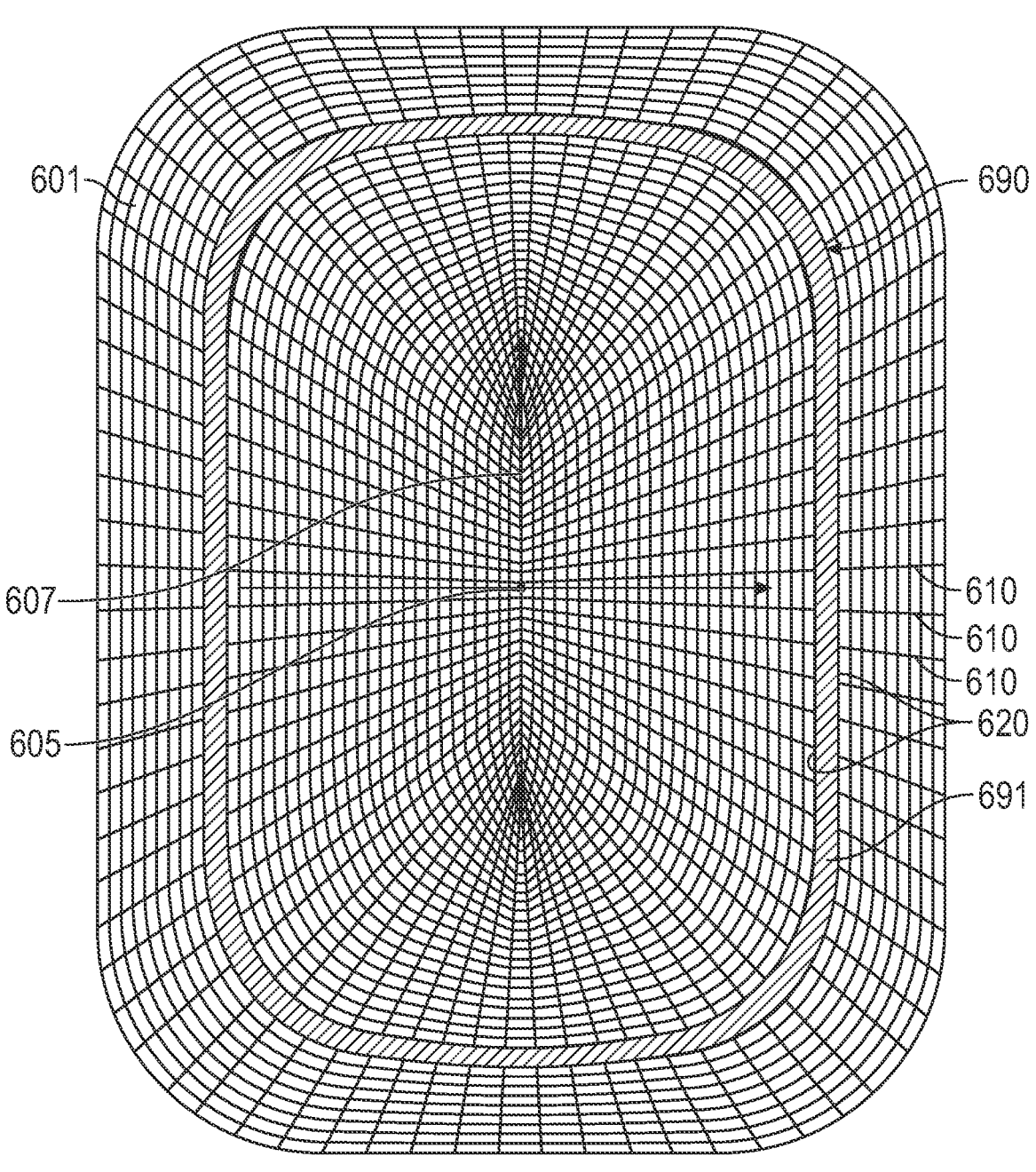

In FIG. 7, implant 600 is shown including web 601 formed from axial yarn 607, radial yarns 610, spiral yarns 620, and at least one reinforcement zone in the shape of a continuous ring 690. Additional first and second threading yarns are also present but not shown in expanded view. In addition, in some embodiments, implant 600 and/or web 601 may further include a substrate, horizontal yarns, vertical yarns, diagonal yarns, framing yarns, and/or mooring yarns.

Reinforcement ring 690 is shown turning around the center 605 and axial yarn 607, as well as extending across the spaces between the radial yarns 610 and the spiral yarns 620 of the web 601. The reinforcement ring 690 is formed by the addition of reinforcing yarns 691 which, like spiral yarns 620, may follow the same continuous path around the center 605 and axial yarn 607 of the web 601 but in a much closer and/or denser manner to produce the reinforcement ring 690. In some embodiments, the reinforcing yarns may be additional spiral yarns 620 in a higher concentration and closer proximity to neighboring spiral yarns 620 to form the ring 690. In some embodiments, the reinforcing yarns may be additional radial yarns 610 in a higher concentration and closer proximity to neighboring radial yarns 610 to form the ring 690. Additional threading yarns may be used to hold the reinforcing yarns 691 in place relative the radial yarns 610 and/or spiral yarns 620.

It is envisioned that the reinforcement ring 690 may stiffen the web 601 and provide the web 601 with the ability to be naturally unroll because the stiffness of the reinforcement ring 690 is greater than the stiffness of the web 601. In addition, since the reinforcement ring 690 is made from reinforcing yarns 691, the reinforcement ring 690 maintains a porosity suitable for promoting tissue ingrowth. Also, the reinforcement ring or zone 690 is configured to strengthen the web 601 for receipt of surgical fasteners, such as sutures, staples, tacks, pins, screws, and the like. In some embodiments, as depicted in FIG. 7, the reinforcement zone 690 does not traverse the axial yarn 610.

As shown in FIG. 2B in the expanded view, and similarly applicable to the web 601 and the laid yarns, i.e., axial yarns, radial yarns, spiral yarns, and/or reinforcing yarns, of FIG. 7 (not shown in expanded view), at least a first threading yarn and a second threading yarn are interlaced to each other to form locking stitches about the laid yarns, i.e., the axial yarns, the radial yarns, the spiral yarns, and/or the reinforcing yarns (not all shown), to hold each of the laid yarns in a position relative to each other to form and/or maintain the overall structure of the reinforcement zones 690 and/or web 601.

Figure 8:
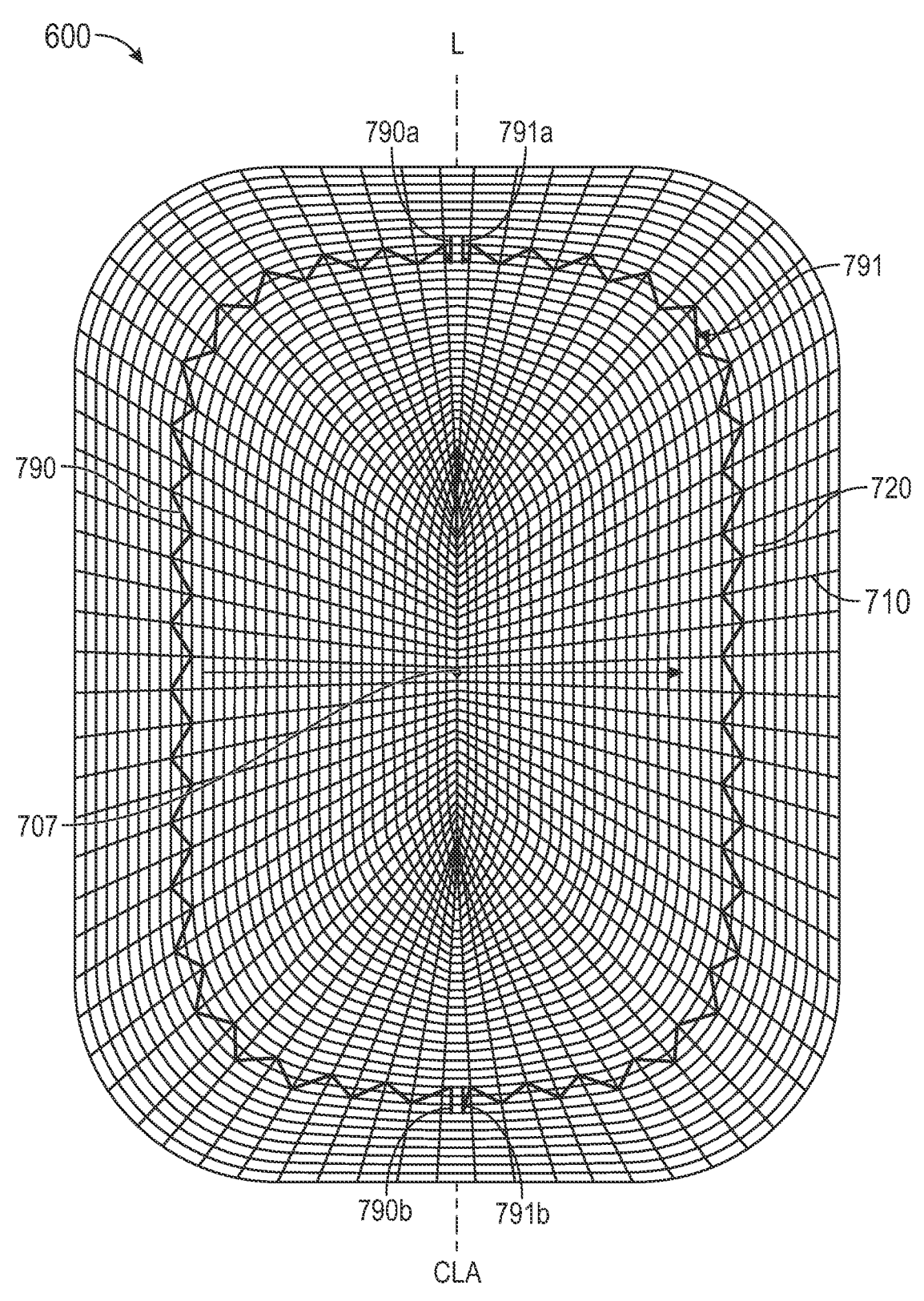

In FIG. 8, implant 700 is shown including web 701 formed from axial yarn 707, radial yarns 710, spiral yarns 720, and a plurality of discontinuous reinforcement rings 790, 791 positioned around the center 705 and axial yarn 707 of the web 701. As shown, a first reinforcement ring 790 is generally C-shaped and faces a second reinforcement ring 791 which is also generally C-shaped. As shown, the generally C-shaped reinforcements may be undulated and/or sinusoidal while extending around the center 705 of the web 701. However, it is also envisioned that the generally C-shaped reinforcement rings may be free of undulations and/or smooth.

The first and second reinforcement rings 790, 791 are spaced apart near their respective end portions 790a-b, 791a-b, to define a fixed folding line L across the surface of the web for folding of the web into two equal halves. As illustrated, at least one of, if not all of, the end portions 790a-b, 791a-b extends parallel to the CLA. In some embodiments, folding line L is positioned along the CLA of web 701 and/or follows the length of axial yarn 707. Additional first and second threading yarns are also present but not shown in expanded view. In addition, in some embodiments, implant 700 and/or web 701 may further include a substrate, horizontal yarns, vertical yarns, diagonal yarns, framing yarns, and/or mooring yarns.

As shown in FIG. 2B in the expanded view, and similarly applicable to the web 701 and the laid yarns, i.e., axial yarns, radial yarns, spiral yarns, and/or reinforcing yarns, of FIG. 8 (not shown in expanded view), at least a first threading yarn and a second threading yarn are interlaced to each other to form locking stitches about the laid yarns, i.e., the axial yarns, the radial yarns, the spiral yarns, and/or the reinforcing yarns, to hold each of the laid yarns in a position relative to each other to form and/or maintain the overall structure of the reinforcement zones 790, 791 and/or web 701.

Figure 9:
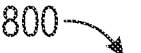

In FIG. 9, implant 800 includes web 801 formed from axial yarn 807, radial yarns 810, and spiral yarns 820 and reinforcement zone 890 which extends longitudinally along a central band of the web 801. Additional first and second threading yarns are also present but not shown in expanded view. In addition, in some embodiments, implant 800 and/or web 801 may further include a substrate, horizontal yarns, vertical yarns, diagonal yarns, framing yarns, and/or mooring yarns.

As depicted, reinforcement zone 890 is in the form of a strip extending from a first peripheral outer edge 815a to a second peripheral outer edge 815b along the axial yarn 807. A higher concentration of axial yarns 807, radial yarns 810, and spiral yarns 820 are found within the reinforcement zone 890. By higher concentration, the respective axial yarns 807, radial yarns 810, and spiral yarns 820 are either thicker in nature than any yarns outside the reinforcement zone 890 and/or closer together and more densely located within the reinforcement zone 890.

In some embodiments, any of the yarns within the reinforcement zones described herein may be made of materials displaying greater tensile strength than the yarns outside the reinforcement zones. In some embodiments, yarns outside the reinforcement zones may be made of materials displaying greater elasticity than the yarns inside the reinforcement zones.

Reinforcement zone 800 may extend a distance d' across central band 806 of 801 web. In some embodiments, the reinforcement zone 890 may extend a distance d' across central band 806 ranging from about 0.05 cm to about 15 cm. In some embodiments, the distance d' ranges from about 0.1 cm to about 12.5 cm. In some embodiments, the distance d' ranges from about 0.25 cm to about 10 cm. In some embodiments, the distance d' ranges from about lcm to about 5 cm. In some embodiments, the distance d' is about 2.5 cm.

As shown in FIG. 2B in the expanded view, and similarly applicable to the web 801 and the laid yarns, i.e., axial yarns, radial yarns, spiral yarns, and/or reinforcing yarns, of FIG. 9 (not shown in expanded view), at least a first threading yarn and a second threading yarn are interlaced to each other to form locking stitches around any combination of the laid yarns, i.e., the axial yarns, the radial yarns, the spiral yarns, and/or the reinforcing yarns (not all shown), to hold each of the laid yarns in a position relative to each other to form and/or maintain the overall structure of the reinforcement zones 890 and/or web 801.

Figure 10:
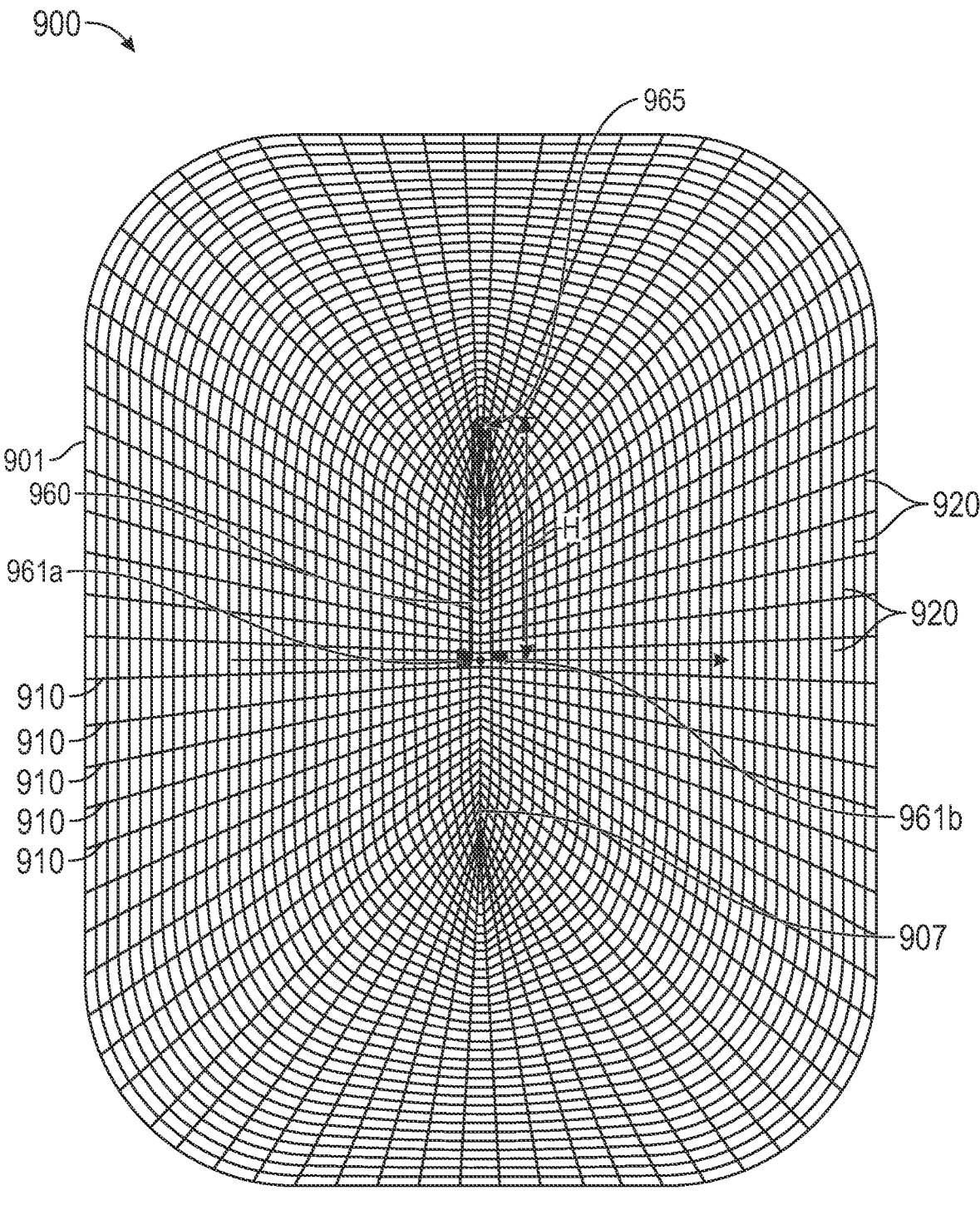
FIGS. 10-11 are top views of surgical implants including a web including laid yarns and threading yarns and at least one suture assembly as described in various embodiments herein.

Turning now to FIG. 10, implant 900 includes web 901 having axial yarn 907, radials yarns 910, spiral yarns 920 and at least one suture assembly 960. Axial yarn 907, radial yarns 910 and spiral yarns 920 are intended to represent any of the axial yarns, radial yarns, and/or spiral yarns described in any of the embodiments described and/or depicted herein. Additional first and second threading yarns are also present but not shown in expanded view. In addition, in some embodiments, implant 900 and/or web 901 may further include a substrate, horizontal yarns, vertical yarns, diagonal yarns, framing yarns, reinforcing yarns, and/or mooring yarns.

Suture assembly 960 includes at least one monofilament or multifilament suture having a first and second end 961a, 961b attached to a surface of the web 901 and forming a suture loop 965 therebetween which is free of web 901. The first and second ends 961a, 961b of the suture assembly 960 can be attached directly to at least one of the axial yarn 907, radial yarns 910, spiral yarns 920, as well as the threading yarns, framing yarns, mooring yarns, reinforcing yarns and combinations thereof.

The suture loop 965 being pivotable about the first and second ends 961a, 961b and relative to the surface of the web 901. In some embodiments, the suture loop 965 extends away from the surface of web 901 in a plane different from the plane that web 901 lies along the longitudinal axis.

As shown, in some embodiments, the first and second ends 961a, 961b of the suture assembly 960 may be centered on at least one face of web 901. As further shown, in some embodiments, the first and second ends 961a, 961b may be attached to the surface of the web 901 along the CTA and/or on opposite sides of axial yarn 907.

In other embodiments, the first and second ends of the suture assembly may be attached directly to a proximal and distal end portions of the axial yarn.

In still other embodiments, the first and second ends of the suture assembly may be attached directly to a pair of radial yarns on opposite sides of the axial yarn thereby allowing the suture loop to traversing the axial yarn.

The suture loop 965 may extend a height H from the face of the web 901. The distance H ranging from about 0.1 cm to about 50 cm, in some embodiments from 0.5 cm to about 40 cm, in some embodiments from about 1 cm to about 30 cm, in some embodiments from about 5 cm to about 25 cm, in some embodiments from about 10 cm to about 20 cm.

In some embodiments, suture loop 965 may be configured to permanently extend generally perpendicular from the surface of the web 901. In some embodiments, suture loop 965 is attached to the at least one surface of the web 901 in a manner configured to allow suture loop 965 to pivot from a flat position extending generally coplanar and/or generally parallel to web 901 to a position generally perpendicular to the plane of the web 901. Suture assembly 960 may be used for the handling and/or anchoring of the web 901, from inside and/or outside the patient's body.

As shown in FIG. 2B in the expanded view, and similarly applicable to the web 901 and the laid yarns, i.e., axial yarns, radial yarns, spiral yarns, and/or reinforcing yarns, of FIG. 10 (not shown in expanded view), at least a first threading yarn and a second threading yarn are interlaced to each other to form locking stitches around any combination of the laid yarns, i.e., the axial yarns, the radial yarns, the spiral yarns, and/or the reinforcing yarns (not all shown), to hold each of the laid yarns in a position relative to each other to form and/or maintain the overall structure of the suture assembly 960 and/or web 901.

Figure 11:
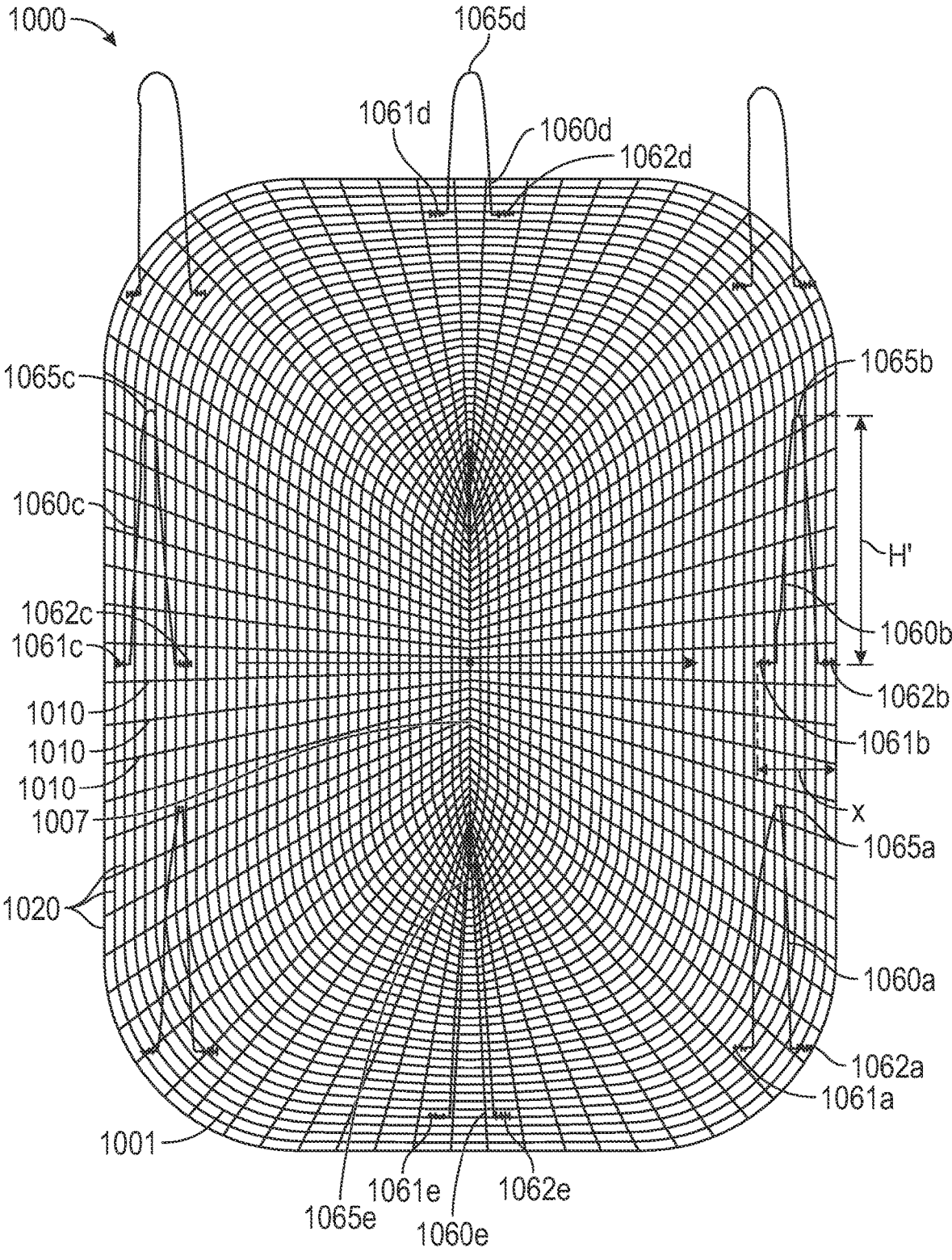

Turning to FIG. 11, implant includes web 1001 formed from axial yarn 1007, radials yarns 1010, spiral yarns 1020 and more than one and/or a plurality of suture assemblies 1060a-e. Axial yarn 1007, radial yarns 1010 and spiral yarns 1020 are intended to represent any of the axial yarns, radial yarns, and/or spiral yarns described in any of the embodiments described and/or depicted herein. In addition, web 1001 may further include a substrate, framing yarns, mooring yarns, reinforcing yarns, and/or first and second threading yarns as also described and/or depicted herein. Each suture assembly 1060a-e includes at least one monofilament or multifilament suture having a first and second end portion 1061a-e, 1062a-e attached to a surface of the web 1001 forming a suture loop 1065 therebetween free of the surface of web 1001.

The first and second ends of the suture assembly can be attached directly to at least one of the axial yarns, radial yarns, spiral yarns, threading yarns, framing yarns, mooring yarns, reinforcing yarns, and combinations thereof.

As shown, in some embodiments, a plurality of suture assemblies 1060a-e and/or suture loops 1065a-e may be positioned on the surface of web 1001 around the axial yarn 1007 and/or along an outer periphery of the surface of web 1001. Any number of suture assemblies is envisioned. The suture assemblies may be positioned symmetrically or asymmetrically around the axial yarn 1007. In addition, it is envisioned that suture assemblies may be positioned on both the center part of the web and the outer periphery.

As shown, in some embodiments, first end portions 1061b-c and second end portions 1062b-c of suture assemblies 1060b-c are attached to radial yarns 1010 on opposite sides of axial yarn 1007. As shown, in some embodiments, first end portions 1061d-e and second end portions 1062d-e of suture assemblies 1060d-e are attached to the same spiral yarns 1020 on opposite sides of the CTA.

The suture loops 1065a-e may extend a distance H from the face of the web 1001. The distance H ranging from about 0.1 cm to about 50 cm, in some embodiments from 0.5 cm to about 40 cm, in some embodiments from about 1 cm to about 30 cm, in some embodiments from about 5 cm to about 25 cm, in some embodiments from about 10 cm to about 20 cm.

In some embodiments, the distance H may be the same for a plurality of the suture loops 1065. In some embodiments, the distance H may be the different for a plurality of the suture loops 1065.

The first end portion 1061*a-e* of each suture assembly 1060*a-e* may be separated a distance x from the respective second end portion 1062*a-e* of each suture assembly 1060*a-e*. The distance x ranging from about 0.1 cm to about 25 cm, in some embodiments from 0.2 cm to about 20 cm, in some embodiments from about 0.3 cm to about 15 cm, in some embodiments from about 0.4 cm to about 10 cm, in some embodiments from about 0.5 cm to about 5 cm. In other embodiments, the distance x is selected from about 0.5 cm, about 0.75 cm, about 1.0 cm, about 1.25 cm, about 1.5 cm, about 1.75 cm, or about 2 cm.

In still other embodiments, the distance x may represent a percentage of the height H. For example, the distance x may range from about 2% to about 98% of the height H, in some embodiments from about 3% to 50%, in some embodiments from about 4% to about 20%, in some embodiments from about 5% about 10%.

In some embodiments, suture loops 1065*a-e* extend generally perpendicular from the surface of the web 1001. In some embodiments, suture loops 1065*a-e* are attached to the at least one surface of the web 1001 in a manner which allows suture loops 1065*a-e* to pivot from a flat position extending generally coplanar and/or generally parallel to web 1001 to a position generally perpendicular to the plane of the web 1001. Suture assembly 1060 may be used for the handling and/or anchoring of the web 1001, from inside and/or outside the patient's body.

As shown in FIG. 2B in the expanded view, and similarly applicable to the web 1001 and the laid yarns, i.e., axial yarns, radial yarns, spiral yarns, and/or reinforcing yarns, of FIG. 11 (not shown in expanded view), at least a first threading yarn and a second threading yarn are interlaced to each other to form locking stitches about any combination of the laid yarns, i.e., the axial yarns, the radial yarns, the spiral yarns, and/or the reinforcing yarns (not all shown), to hold each of the laid yarns in a position relative to each other to form and/or maintain the overall structure of the suture assembly 1060 and/or web 1001.

Figure 12A:
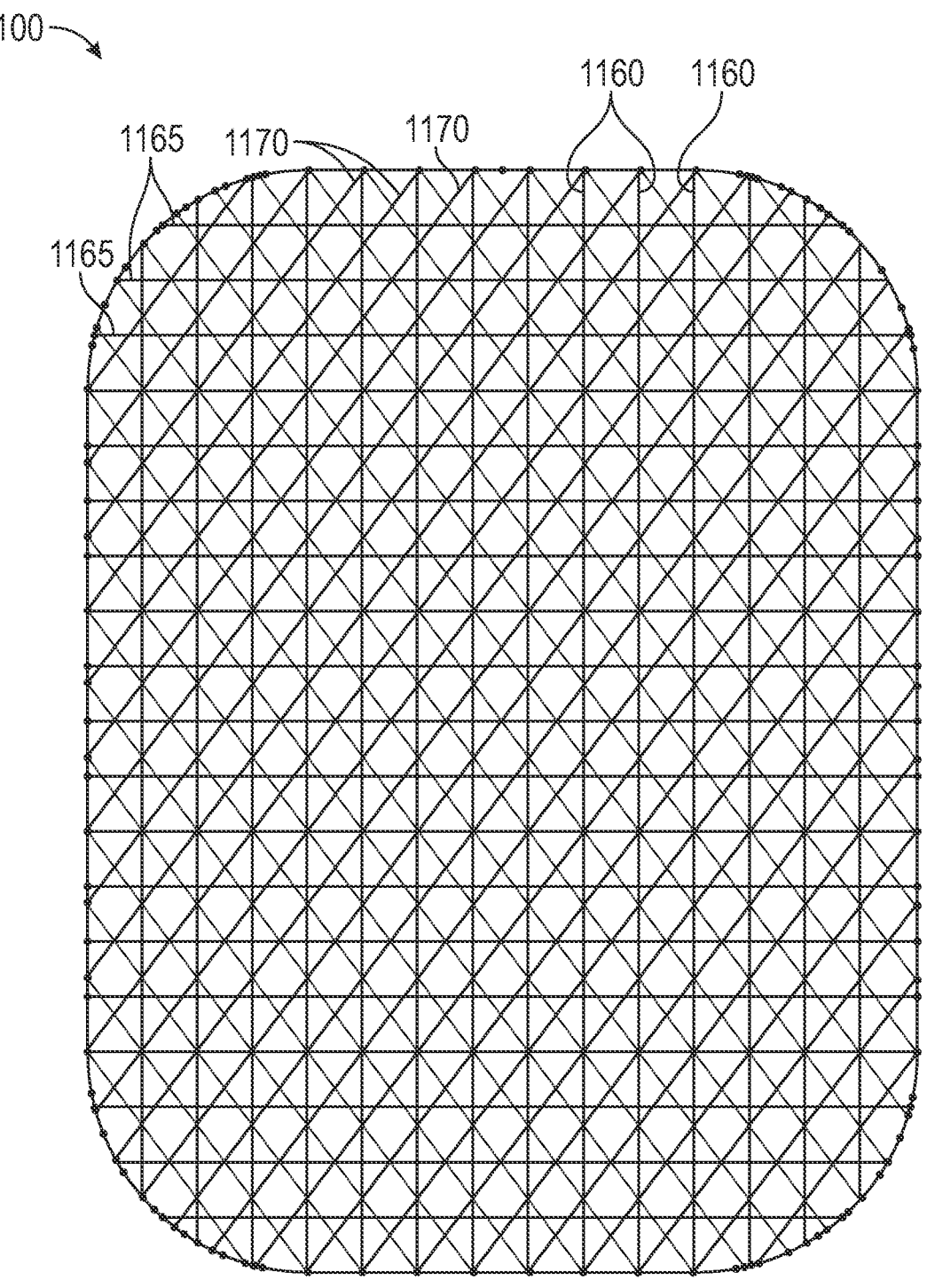
FIGS. 12A-12C are top views of surgical implants including a web including laid yarns and threading yarns as described in various embodiments herein.

FIG. 12A depicts a web 1100 as described herein including vertical 1160, horizontal 1165, and diagonal yarns 1170 prior to being combined with any combination of other laid yarns as described herein. FIG. 12A is not intended to be indicative that the horizontal, vertical, and/or diagonal yarns have to be laid prior to the other yarns. Rather, FIG. 12A is simply intended to offer a clearer look at the horizontal, vertical, and diagonal yarns and to simplify the figures by not overly crowding the figures with every yarn and/or line. Although the vertical and and/or horizontal yarns may resemble a pattern found in some conventional textiles or mesh, such as warp and weft yarns, the vertical, horizontal, and diagonal yarns are not interwoven like conventional textiles or mesh. Rather, as explained throughout the present disclosure, the vertical, horizontal, and diagonal laid yarns are free-flowing until threading yarns are added to secure and lock into the laid yarns into position.

Figure 12B:
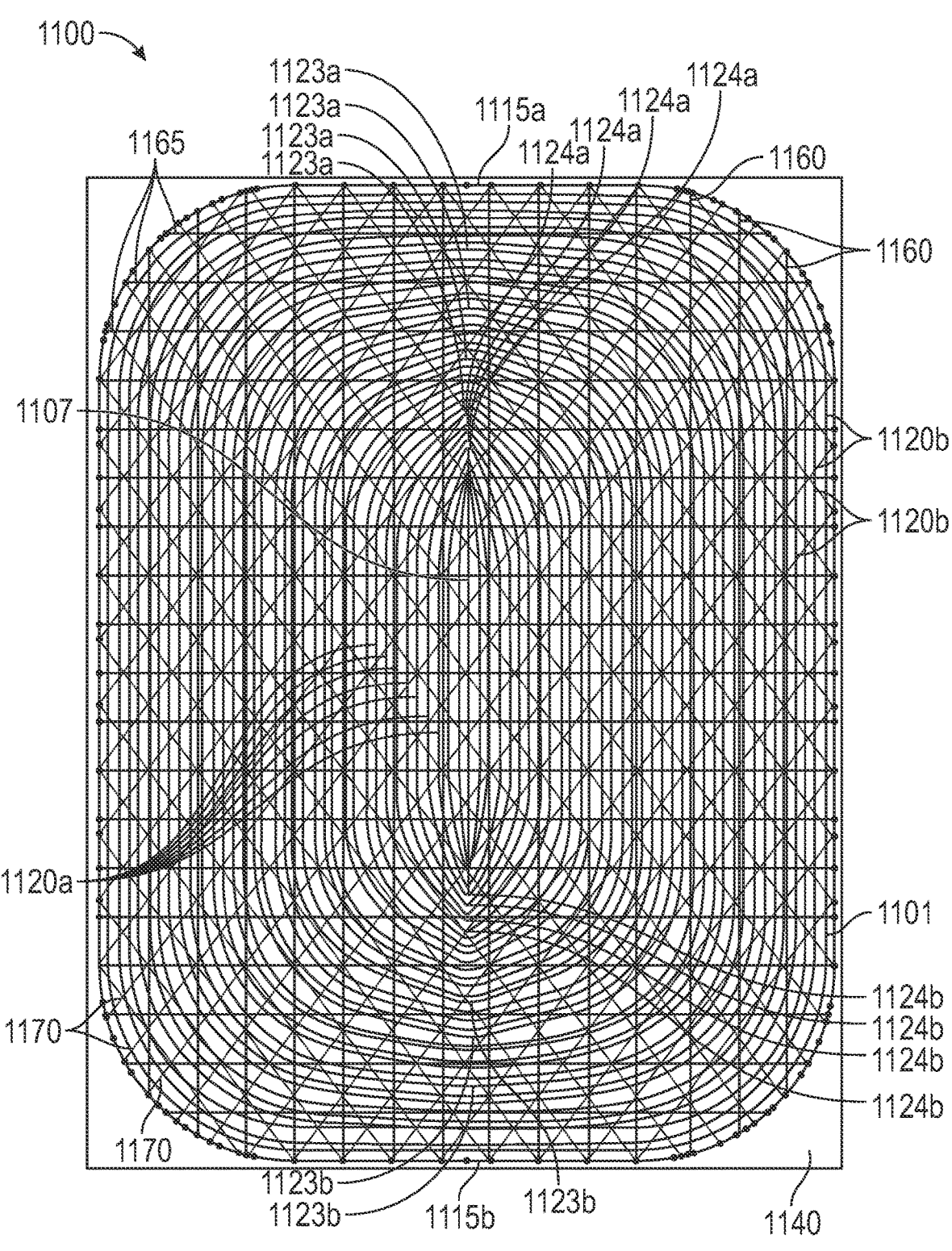
Figure 12C:
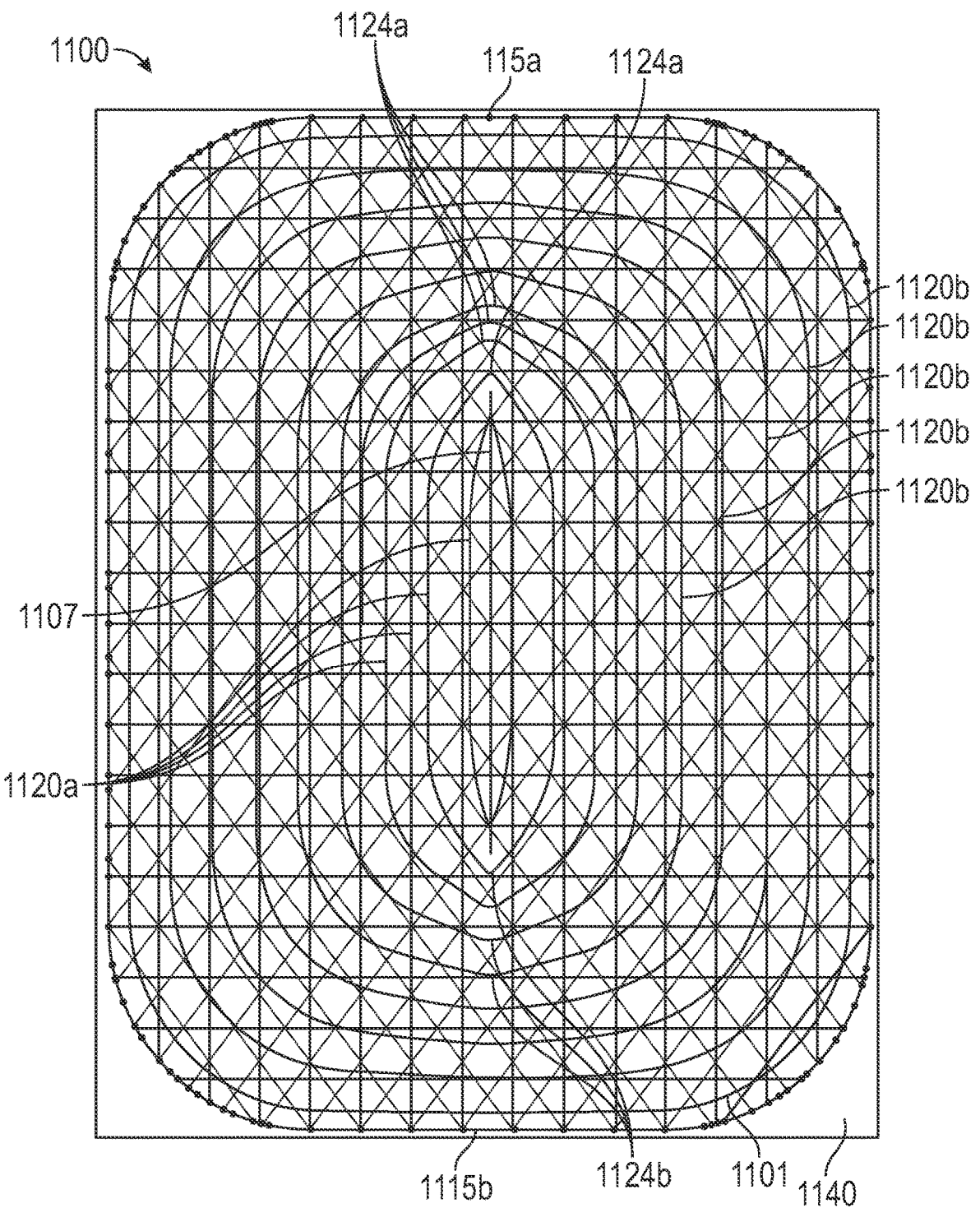

FIGS. 12B-12C depict implant 1100 including a web 1101 attached on top of substrate 1140. Web 1101 includes axial yarn 1107, spiral yarns 1120*a-b*, vertical yarns 1160, horizontal yarns 1165, and diagonal yarns 1170. Radial yarns are not depicted in FIGS. 12B and 12C in an effort to simplify the figures by not overly crowding the figures with every yarn and/or line. Additional first and second threading yarns are also present but not depicted for similar reasons. However, both the radial yarns and threading yarns that may be used are described elsewhere in the present disclosure. In addition, in some embodiments, implant 1100 and/or web 1101 may further include framing yarns and/or mooring yarns.

In some embodiments, the implants of FIGS. 12B-12C may include radial yarns. In some embodiments, the implants of FIGS. 12B-12C may not include radial yarns.

As shown in FIGS. 12B-12C, the innermost spiral yarns 1120*a* (closest to the axial yarn) can form the general shape of an ellipse, with two opposite long sides 1123*a*, which are substantially parallel to the axial yarn 1107, connected to the two opposite short sides 1123*b*, which are substantially perpendicular to the axial yarn 1107, wherein in each of the short sides 1123*b* of form a first and second U-shaped bend 1124*a*, 1124*b* extending around the axial yarn 1107 towards the outer peripheral edges 1115*a*, 1115*b*, respectively.

As further shown in FIGS. 12B-12C, in some embodiments, the outermost spiral yarns 1120*b* (furthest from the axial yarn) do not include the U-shaped bends along the short side of the loop. In such embodiments, the general contour of the innermost spiral yarns 1120*a* may differ from the general contour of the outermost spiral yarns 1120*b*.

FIG. 12C differs from FIG. 12B in that the concentration of the spiral yarns 1120*a-b* are less than those depicted in FIG. 12B, and specifically every other spiral yarn 1120 was removed for both clarity of the figures and to show any concentration of spiral yarns may be used.

As shown in FIG. 2B in the expanded view, and similarly applicable to the web 1101 and the laid yarns, i.e., axial yarns, radial yarns, spiral yarns, vertical yarns, horizontal yarns, diagonal yarns, and/or reinforcing yarns, of FIGS. 12B-12C (not shown in expanded view), at least a first threading yarn and a second threading yarn are interlaced to each other to form locking stitches about the laid yarns, i.e., the axial yarns, the radial yarns, the spiral yarns, the horizontal yarns, the vertical yarns, the diagonal yarns, and/or the reinforcing yarns (not all shown), to hold each of the laid yarns in a position relative to each other to form and/or maintain the overall structure of the web 1101.

Figure 13A:
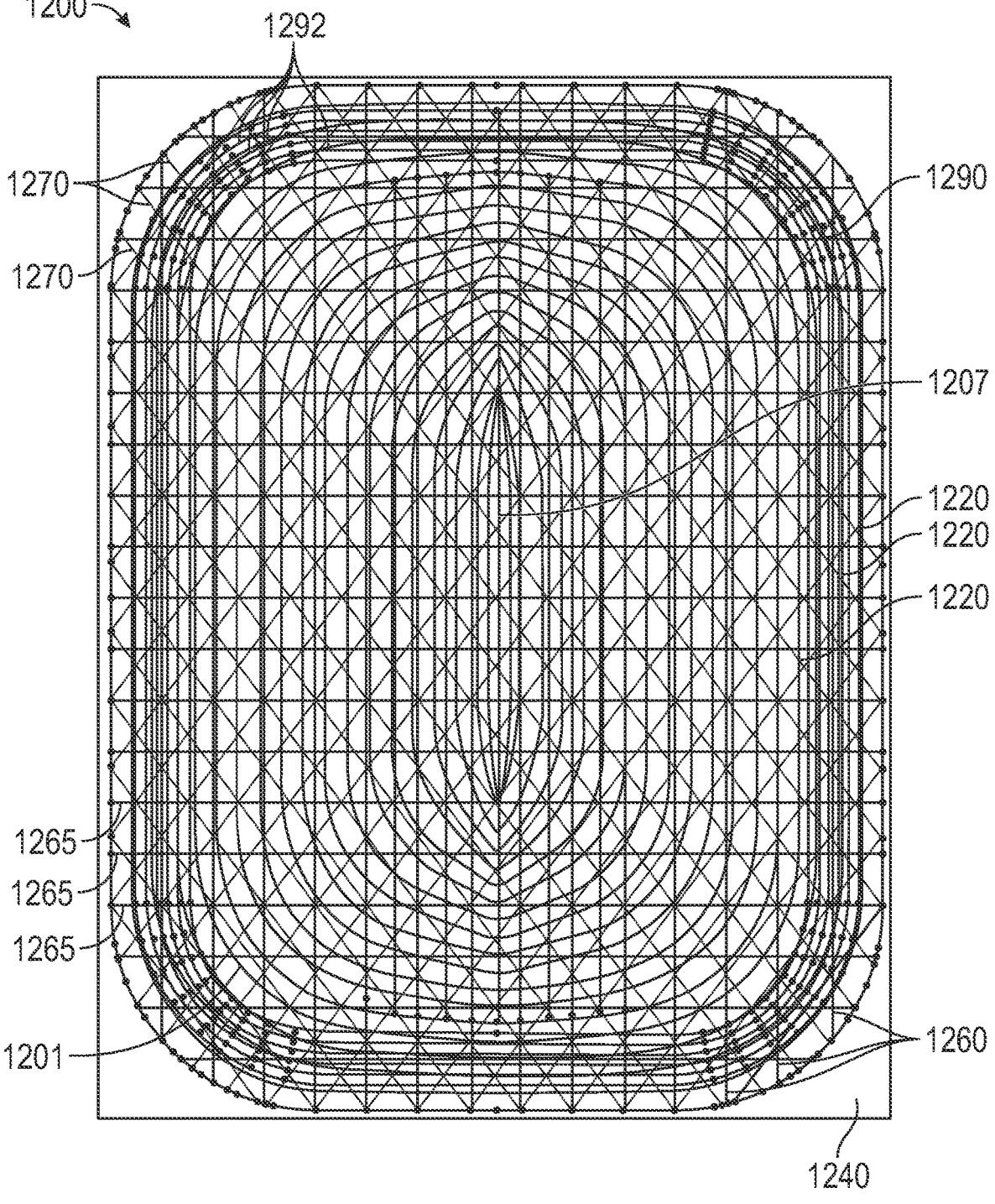
FIGS. 13A-13B are top views of surgical implants including a web including laid yarns and threading yarns and at least one reinforcing zone as described in various embodiments herein.
Figure 13B:
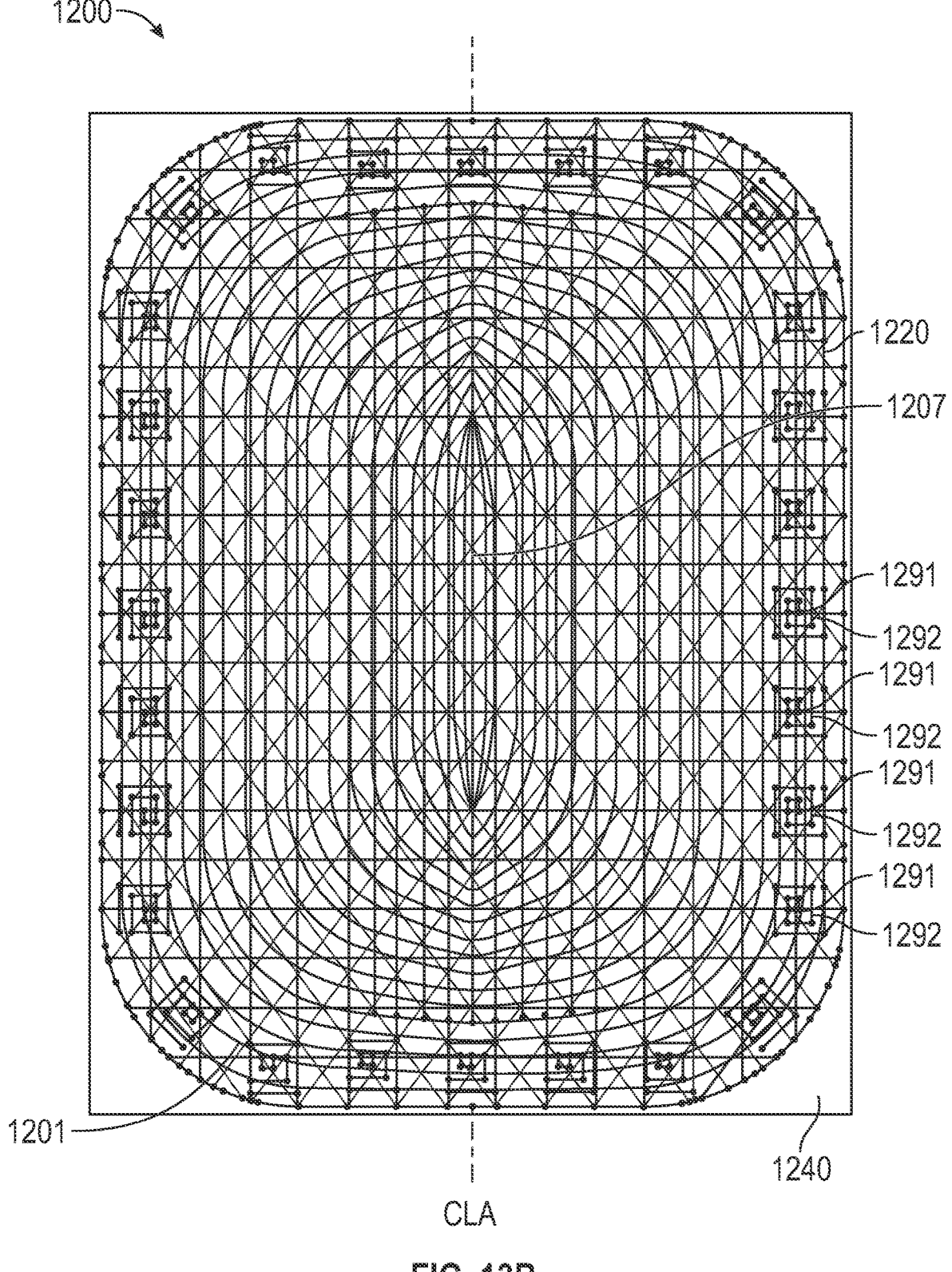

FIGS. 13A and 13B depict an implant 1200 including a web 1201 attached to a substrate 1240, wherein the implant further includes axial yarn 1207, spiral yarns 1220, reinforcing members or zones 1290, 1291, vertical yarns 1260, horizontal yarns 1265, and diagonal yarns 1270. Radial yarns are not depicted in FIGS. 13B and 13C in an effort to simplify the figures by not overly crowding the figures with every yarn and/or line. Additional first and second threading yarns are also present but not depicted for similar reasons. However, both the radial yarns and threading yarns that may be used are described elsewhere in the present disclosure. In addition, in some embodiments, implant 1200 and/or web 1201 may further include framing yarns and/or mooring yarns.

As depicted in FIG. 13A, reinforcing zone 1290 is in the form of a continuous ring around the axial yarn 1207 on the outer peripheral edge of implant 1200. However, it is envisioned that any of the reinforcement zones described and/or depicted herein may be equally applicable to be added to web 1201 in forming implant 1200.

In some embodiments, as illustrated, the reinforcing zone 1290 may include a plurality of reinforcing yarns 1292 following a path similar to the spiral yarns 1220 around the axial yarn 1207, however, the concentration of reinforcing yarns 1292 is significantly higher and/or denser on the face of the web 1201, as compared to the spiral yarns 1207. In addition, the radial distance between neighboring reinforcing yarns 1292 is significantly less than the radial distance between neighboring spiral yarns 1220.

As depicted in FIG. 13B, reinforcing zones 1291 are in the form of a plurality of discontinuous tabs positioned around the axial yarn 1207 on the outer peripheral edge of implant 1200. However, it is envisioned that any of the reinforcement zones described and/or depicted herein may be equally applicable to be added to web 1201 in forming implant 1200.

In some embodiments, as illustrated, the reinforcing zones 1291 may include a plurality of reinforcing yarns 1294 following a path dissimilar to any path taking by the radial yarns and/or the spiral yarns 1220 around the axial yarn 1207. In some embodiments, the reinforcing yarns 1294 may follow a path parallel to and/or perpendicular to the CLA in forming the reinforcement zones.

As shown in FIG. 2B in the expanded view, and similarly applicable to the web 1201 and the laid yarns, i.e., axial yarns, radial yarns, spiral yarns, and/or reinforcing yarns, of FIGS. 13A-13C (not shown in expanded view), at least a first threading yarn and a second threading yarn are interlaced to each other to form locking stitches about the laid yarns, i.e., the axial yarns, the radial yarns, the spiral yarns, the horizontal yarns, the vertical yarns, the diagonal yarns, and/or the reinforcing yarns (not all shown), to hold each of the laid yarns in a position relative to each other to form and/or maintain the overall structure of the web 1201.

Figures 14A, 14B:
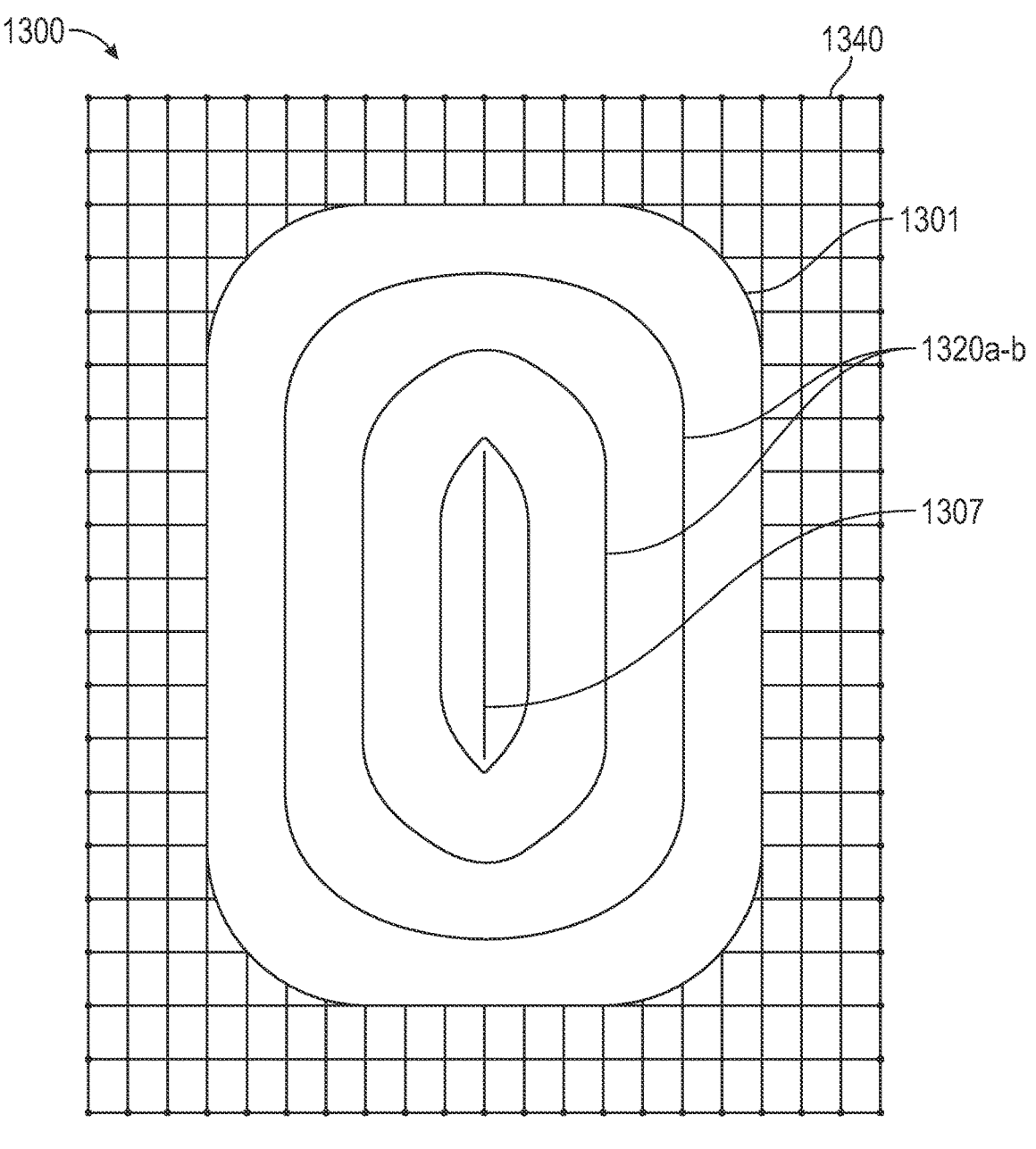
FIGS. 14A-14B are top views of surgical implants including a web including laid yarns and threading yarns and a substrate as described in various embodiments herein.

As depicted in FIG. 14A, an implant 1300 including a web 1301 attached to a substrate 1340, wherein substrate 1340 is surgical mesh made from knitting, braiding, or weaving. In particular embodiments, substrate 1340 is knit mesh. The knit mesh may be a two-or three-dimensional knit mesh or a combination of both. The knit mesh may include spiked naps on at least one side, such as a Pro-Grip® mesh.

FIG. 14A depicts implant 1300 including a web 1301 attached on top of substrate 1340. Web 1301 may include any combination of laid yarns described herein. As shown, in some embodiments, the web 1301 may include at least an axial yarn 1307 and spiral yarns 1320*a-b*. Radial yarns, vertical yarns, horizontal yarns, diagonal yarns and reinforcing yarns are not depicted in FIGS. 14A and 14B in an effort to simplify the figures by not overly crowding the figures with every yarn and/or line. Additional first and second threading yarns are present but not depicted for similar reasons. However, the radial yarns, vertical yarns, horizontal yarns, and diagonal yarns, threading yarns, and reinforcing zones that may be used are described elsewhere in the present disclosure. In addition, in some embodiments, implant 1300 and/or web 1301 may further include framing yarns and/or mooring yarns.

In some embodiments, the implants of FIGS. 14A-14B may include radial yarns as described herein. In some embodiments, the implants of FIGS. 14A-14B may not include radial yarns as described herein.

In some embodiments, the implants of FIGS. 14A-14B may include reinforcing yarns or reinforcing zones as described herein. In some embodiments, the implants of FIGS. 14A-14B may not include reinforcing yarns or reinforcing zones as described herein.

In some embodiments, the implants of FIGS. 14A-14B may include vertical yarns, horizontal yarns, and diagonal yarns as described herein. In some embodiments, the implants of FIGS. 14A-14B may not include vertical yarns, horizontal yarns, and diagonal yarns zones as described herein.

As shown in FIG. 14B, substrate 1340 is a knit mesh including spiked naps 1345 on a first side of the substrate and a web 1301 positioned on a second opposite side of substrate 1345, opposite the spiked naps 1345. Although depicted on opposite sides of the substrate, it is envisioned that in some embodiments, the web and the spiked naps may be on the same side and/or both sides of the substrate.

As shown in FIG. 2B in the expanded view, and similarly applicable to the web 1301 and the laid yarns, i.e., axial yarns, radial yarns, spiral yarns, vertical yarns, horizontal yarns, diagonal yarns, and/or reinforcing yarns, of FIGS. 14A and 14B (not shown in expanded view), at least a first threading yarn and a second threading yarn are interlaced to each other to form locking stitches about the laid yarns, i.e., the axial yarns, the radial yarns, the spiral yarns, vertical yarns, horizontal yarns, diagonal yarns, and/or the reinforcing yarns (not all shown), to hold each of the laid yarns in a position relative to each other to form and/or maintain the overall structure of the web 1301.

Figure 15:
FIG. 15 is a top view of surgical implants including a web including laid yarns and threading yarns as described in various embodiments herein; and, FIG. 16 is a top view of surgical implants including a web including laid yarns and threading yarns as described in various embodiments herein.

Turning to FIG. 15, in some embodiments, the implant 1400 may include a web 1401 including at least one axial yarn 1407, radial yarn 1410, spiral yarn 1420, and at least one radial loop 1411. As depicted, in some embodiments, a radial yarn 1410 may be laid to extend from a first portion 1407*a* of the axial yarn 1407 to beyond the outermost spiral yarn 1420*a* and return back to a second portion 1407*b* of the axial yarn 1407 forming a radial loop 1411 positioned beyond the outermost spiral yarn 1420*a*. The radial loop 1411 may provide the web 1401 with an area beyond the outermost spiral yarn 1420*a* which is suitable for anchoring the web into tissue via conventional means, such as staples, screws, pins, tacks, sutures, adhesives, and the like.

As further depicted in FIG. 15, in some embodiments, the axial, radial, and spiral yarns may be laid as separate layers on top of each other thereby creating a web having a thickness generally equal to the sum of the thickness of each of the laid yarns. For example, the web may have a first layer including only the at least one spiral yarn, a second layer including only the radial yarns laid on top of the spiral yarns, and a third layer including only the axial yarn laid on top of the radial yarns. It is envisioned that the axial, radial and spiral yarns may be layered in any order. It is further envisioned that in other embodiments, any of the laid yarns described herein may also be layered separately from each other when forming a web.

As shown in FIG. 2B in the expanded view, and similarly applicable to the web 1401 and the laid yarns, i.e., axial yarns, radial yarns, and/or spiral yarns, of FIG. 15 (not shown in expanded view), at least a first threading yarn and a second threading yarn are interlaced to each other to form locking stitches around any combination of the laid yarns, i.e., the axial yarns, the radial yarns, the spiral yarns, vertical yarns, horizontal yarns, diagonal yarns, and/or the reinforcing yarns (not all shown), to hold each of the laid yarns in a position relative to each other to form and/or maintain the overall structure of the web 1401.

Figure 16:
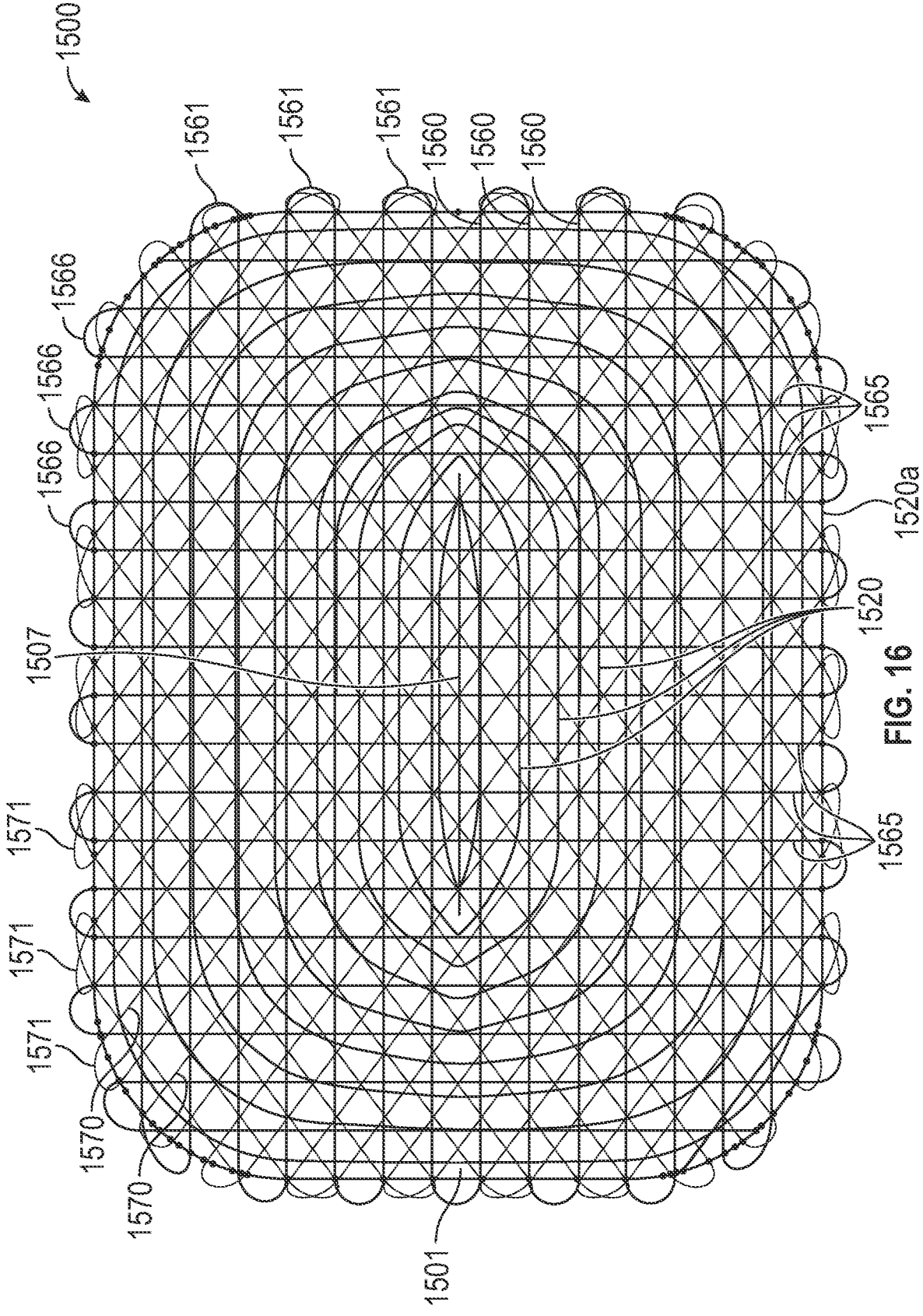

FIG. 16 illustrates an implant 1500 including a web 1501 including axial yarn 1507, spiral yarns 1520 including outermost spiral yarn 1520*a*, vertical yarns 1560, horizontal yarns 1565, and diagonal yarns 1570, wherein at least some of the vertical yarns 1560 extend beyond the outermost spiral yarn 1520*a* to form vertical loops 1561, the horizontal yarns 1565 extend beyond the outermost spiral yarn 1520*a* to form horizontal loops 1566, and/or the diagonal yarns 1570 extend beyond the outermost spiral yarn 1520*a* to form diagonal loops 1571. Any of the vertical, horizontal or diagonal loops 1561, 1565, 1571, respectively may provide the web 1501 with an area beyond the outermost spiral yarn 1520*a* which is suitable for anchoring the web into tissue via conventional means, such as staples, screws, pins, tacks, sutures, adhesives, and the like.

In some embodiments, the vertical loops 1561 may extend a greater distance from the outermost spiral yarn 1520*a* than the horizontal loops 1566 and diagonal loops 1571.

In some embodiments, the horizontal loops 1566 may extend a greater distance from the outermost spiral yarn 1520*a* than the vertical loops 1561 and diagonal loops 1571.

In some embodiments, the diagonal loops 1571 may extend a greater distance from the outermost spiral yarn 1520*a* than the vertical loops 1561 and horizontal loops 1566.

As shown in FIG. 2B in the expanded view, and similarly applicable to the web 1501 and the laid yarns, i.e., axial yarns, horizontal yarns, vertical yarns, diagonal yarns, and/or spiral yarns, of FIG. 16 (not shown in expanded view), at least a first threading yarn and a second threading yarn are interlaced to each other to form locking stitches around any combination of the laid yarns, i.e., the axial yarns, the radial yarns, the spiral yarns, vertical yarns, horizontal yarns, diagonal yarns, and/or the reinforcing yarns (not all shown), to hold each of the laid yarns in a position relative to each other to form and/or maintain the overall structure of the web 1501.

While the present implants and/or implantable webs have been described in connection with a number of exemplary embodiments, and implementations, the present implants and/or implantable webs are not so limited, but rather cover various modifications, and equivalent arrangements.

EXAMPLES

Example 1

An implantable web was prepared using TFP technology as described herein to place and secure monofilament radial yarns, monofilament spiral yarns, and a monofilament axial yarn, onto a dissolvable substrate via the interlacing of first and second multifilament threading yarns. The radial and axial monofilament yarns were made of a copolymer of polytetrahydrofurane and polybutylene terephthalate (TPC), each having a diameter of 210 µm. The spiral monofilament yarns were made of polypropylene (PP) and had a diameter of 300 µm. The first and second threading multifilament yarns were made of 30 Tex polyethylene terephthlate (PET). The dissolvable substrate was made of a non-woven water-soluble polyvinyl alcohol (PVA).

Example 2

An implantable web was prepared using TFP technology as described herein to place and secure monofilament radial yarns, monofilament spiral yarns, and a monofilament axial yarn, onto a dissolvable substrate via the interlacing of first and second multifilament threading yarns. The radial and axial monofilament yarns were made of a copolymer of polytetrahydrofurane and polybutylene terephthalate (TPC), each having a diameter of 400 µm. The spiral monofilament yarns were made of polypropylene (PP) and had a diameter of 300 µm. The first and second threading multifilament yarns were made of 30 Tex polyethylene terephthalate (PET).

The dissolvable substrate was made of a non-woven water-soluble polyvinyl alcohol (PVA).

Example 3

An implantable web was prepared using TFP technology as described herein to place and secure monofilament vertical yarns, monofilament horizontal yarns, monofilament diagonal yarns, and monofilament spiral yarns, onto a dissolvable substrate via the interlacing of first and second multifilament threading yarns. The horizontal, vertical and diagonal monofilament yarns were made of a copolymer of polytetrahydrofurane and polybutylene terephthalate (TPC), each having a diameter of 210 µm. The spiral monofilament yarns were made of polypropylene (PP) and had a diameter of 300 µm. The first and second threading multifilament yarns were made of 30 Tex polyethylene terephthlate (PET). The dissolvable substrate was made of a non-woven water-soluble polyvinyl alcohol (PVA).

Example 4

An implantable web was prepared using TFP technology as described herein to place and secure monofilament vertical yarns, monofilament horizontal yarns, monofilament diagonal yarns, and monofilament spiral yarns, onto a dissolvable substrate via the interlacing of first and second monofilament threading yarns. The horizontal, vertical and diagonal monofilament yarns were made of a copolymer of polytetrahydrofurane and polybutylene terephthalate (TPC), each having a diameter of 210 µm. The spiral monofilament yarns were made of polypropylene (PP) and had a diameter of 300 µm. The first and second threading monofilament yarns were made of 100 µm polypropylene (PP). The dissolvable substrate was made of a non-woven water-soluble polyvinyl alcohol (PVA).

Example 5

An implantable web was prepared using TFP technology as described herein to place and secure monofilament vertical yarns, monofilament horizontal yarns, monofilament diagonal yarns, and monofilament spiral yarns, onto a dissolvable substrate via the interlacing of first and second monofilament threading yarns. The horizontal, vertical and diagonal monofilament yarns were made of a copolymer of polytetrahydrofurane and polybutylene terephthalate (TPC), each having a diameter of 210 µm. The spiral monofilament yarns were made of polypropylene (PP) and had a diameter of 300 µm. The first and second threading multifilament yarns were made of 108 Dtex polyethylene terephthlate (PET). The dissolvable substrate was made of a non-woven water-soluble polyvinyl alcohol (PVA).

Example 6

An implantable web was prepared using TFP technology as described herein to place and secure monofilament vertical yarns, monofilament horizontal yarns, monofilament diagonal yarns, and monofilament spiral yarns, onto a knitted mesh via the interlacing of first and second multifilament threading yarns. The horizontal, vertical and diagonal monofilament yarns were made of a copolymer of polytetrahydrofurane and polybutylene terephthalate (TPC), each having a diameter of 210 µm. The spiral monofilament yarns were made of polypropylene (PP) and had a diameter of 300 µm. The first and second threading multifilament yarns were made of 30 Tex polyethylene terephthlate (PET). The knitted mesh was made of a non-absorbable monofilament textile with an absorbable monofilament grip member on the textile.

Example 7

An implantable web was prepared using TFP technology as described herein to place and secure monofilament vertical yarns, monofilament horizontal yarns, monofilament diagonal yarns, and monofilament spiral yarns, onto a knitted mesh via the interlacing of first and second monofilament threading yarns. The horizontal, vertical and diagonal monofilament yarns were made of a copolymer of polytetrahydrofurane and polybutylene terephthalate (TPC), each having a diameter of 210 μm. The spiral monofilament yarns were made of polypropylene (PP) and had a diameter of 300 μm. The first and second threading monofilament yarns were made of 100 μm polypropylene (PP). The knitted mesh was made of a non-absorbable monofilament textile with an absorbable monofilament grip member on the textile.

Example 8

An implantable web was prepared using TFP technology as described herein to place and secure monofilament vertical yarns, monofilament horizontal yarns, monofilament diagonal yarns, and monofilament spiral yarns, onto a knitted mesh via the interlacing of first and second monofilament threading yarns. The horizontal, vertical and diagonal monofilament yarns were made of a copolymer of polytetrahydrofurane and polybutylene terephthalate (TPC), each having a diameter of 210 μm. The spiral monofilament yarns were made of polypropylene (PP) and had a diameter of 300 μm. The first and second threading multifilament yarns were made of 108 Dtex polyethylene terephthlate (PET). The knitted mesh was made of a non-absorbable monofilament textile with an absorbable monofilament grip member on the textile.

Example 9

An implantable web was prepared using TFP technology as described herein to place and secure monofilament vertical yarns, monofilament horizontal yarns, monofilament diagonal yarns, and monofilament spiral yarns, onto a dissolvable substrate via the interlacing of first and second multifilament threading yarns. The horizontal, vertical and diagonal monofilament yarns were made of a copolymer of polytetrahydrofurane and polybutylene terephthalate (TPC), each having a diameter of 210 μm. The spiral monofilament yarns were made of polypropylene (PP) and had a diameter of 300 μm. The first and second threading multifilament yarns were made of 108 Dtex polyethylene terephthlate (PET). The dissolvable substrate was made of a non-woven water-soluble polyvinyl alcohol (PVA).

Example 10

An implantable web was prepared using TFP technology as described herein to place and secure monofilament vertical yarns, monofilament horizontal yarns, monofilament diagonal yarns, and monofilament spiral yarns, onto a dissolvable substrate via the interlacing of first and second multifilament threading yarns. The horizontal, vertical and diagonal monofilament yarns were made of a copolymer of polytetrahydrofurane and polybutylene terephthalate (TPC), each having a diameter of 400 μm. The spiral monofilament yarns were made of polypropylene (PP) and had a diameter of 300 μm. The first and second threading multifilament yarns were made of 108 Dtex polyethylene terephthlate (PET). The dissolvable substrate was made of a non-woven water-soluble polyvinyl alcohol (PVA).

Example 11

An implantable web was prepared using TFP technology as described herein to place and secure monofilament vertical yarns, monofilament horizontal yarns, monofilament diagonal yarns, and monofilament spiral yarns, onto a knitted mesh via the interlacing of first and second multifilament threading yarns. The horizontal, vertical and diagonal monofilament yarns were made of a copolymer of polytetrahydrofurane and polybutylene terephthalate (TPC), each having a diameter of 210 μm. The spiral monofilament yarns were made of polypropylene (PP) and had a diameter of 300 μm. The first and second threading multifilament yarns were made of 108 Dtex polyethylene terephthlate (PET). The knitted mesh was made a non-absorbable monofilament textile with an absorbable monofilament grip member.

Example 12

An implantable web was prepared using TFP technology as described herein to place and secure monofilament vertical yarns, monofilament horizontal yarns, monofilament diagonal yarns, and monofilament spiral yarns, onto a knitted mesh via the interlacing of first and second multifilament threading yarns. The horizontal, vertical and diagonal monofilament yarns were made of a copolymer of polytetrahydrofurane and polybutylene terephthalate (TPC), each having a diameter of 400 μm. The spiral monofilament yarns were made of polypropylene (PP) and had a diameter of 300 μm. The first and second threading multifilament yarns were made of 108 Dtex polyethylene terephthlate (PET). The knitted mesh was made of a non-absorbable monofilament textile with an absorbable monofilament grip member.

What is claimed is:

1. A method of forming an implantable web for soft tissue repair comprising the steps of:
   a) providing a substrate onto a movable tray,
   b) laying a plurality of laid yarns onto a first side of a substrate via a laying guide element, wherein the laid yarns includes a plurality of radial yarns and a plurality of spiral yarns, each of the plurality of radial yarns extending in a radial direction from a center of a central area of the implantable web, and each of the plurality of spiral yarns turning around the central area and extending between the plurality of radial yarns, the spiral yarns connecting neighboring radial yarns
   c) threading a needle including a first threading yarn from the first side of the substrate through the substrate to a second side of the substrate and around a second threading yarn,
   d) returning the needle to the first side of the substrate with a portion of the first and second threading yarns to form a locking stitch around at least one of the plurality of laid yarns and locking the laid yarn into position on the substrate and relative to other laid yarns,
   e) advancing some combination of the movable tray, substrate, laying guide element, or needle to extend the first and second threading yarns along the laid yarn a certain length before repeating steps c) and d), wherein the threading yarns are smaller in cross-sectional size than the radial yarns, which are smaller in cross-sectional size than the spiral yarns.

2. The method of claim 1, wherein the substrate is dissolvable.

3. The method of claim 1, wherein the substrate is a knit textile.

4. The method of claim 3, wherein the knit textile includes a plurality of spiked naps extending from at least one face thereof.

5. The method of claim 1, wherein the substrate is larger in surface area than the implantable web thereby expanding beyond an outer peripheral edge of the implantable web to define an outer peripheral edge of an implant.

6. The method of claim 1, wherein tailor fiber placement technology is used in forming the implantable web.

7. The method of claim 1, wherein threading the needle including the first threading yarn through the substrate further comprises passing the needle into a thread bobbin including the second threading yarn.

8. The method of claim 7, wherein the thread bobbin further comprises a movable shuttle hook configured to catch the first threading yarn and carry the first threading yarn around the second threading yarn.

9. The method of claim 1, wherein the laying guide element is configured to rotate 360 degrees.

10. The method of claim 1, further comprising f) removing the substrate from the web prior to implantation.

11. The method of claim 1, wherein the laid yarns further include yarns selected from the group consisting of axial yarns, framing yarns, mooring yarns, vertical yarns, horizontal yarns, diagonal yarns, reinforcing yarns, and combinations thereof.

12. The method of claim 1, wherein at least one of the laid yarns and the threading yarns is a monofilament.

13. The method of claim 1, wherein at least one of the laid yarns and the threading yarns is a multifilament.

14. The method of claim 1, wherein at least one of the laid yarns and the threading yarns is made of an absorbable material.

15. The method of claim 1, wherein at least one of the laid yarns and the threading yarns is made of a non-bioabsorbable material.

16. The method of claim 1, wherein at least one locking stitch is formed on a length of each of the radial yarns positioned between each intersection where the radial yarn crisscrosses the spiral yarn.

17. The method of claim 1, wherein at least one locking stitch is formed on a length of each of the spiral yarns positioned between each intersection where the spiral yarn crisscrosses the radial yarn.

* * * * *